(12) United States Patent
Baker et al.

(10) Patent No.: US 10,342,903 B2
(45) Date of Patent: *Jul. 9, 2019

(54) IRRIGATION AND ASPIRATION DEVICE AND METHOD

(71) Applicant: Aardvark Medical, Inc., Ross, CA (US)

(72) Inventors: Peter C. Baker, Ross, CA (US); Clinton N. Slone, San Francisco, CA (US); Michael J. Strasser, San Francisco, CA (US); James M. Lovette, Half Moon Bay, CA (US)

(73) Assignee: Aardvark Medical, Inc., Ross, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/818,048

(22) Filed: Nov. 20, 2017

(65) Prior Publication Data

US 2018/0071442 A1    Mar. 15, 2018

Related U.S. Application Data

(63) Continuation of application No. 15/623,287, filed on Jun. 14, 2017, now Pat. No. 9,844,613, which is a
(Continued)

(51) Int. Cl.
*A61M 1/00* (2006.01)
*A61M 3/02* (2006.01)
*A61B 17/24* (2006.01)

(52) U.S. Cl.
CPC .......... *A61M 1/0084* (2013.01); *A61B 17/24* (2013.01); *A61M 1/0058* (2013.01); *A61M 1/0062* (2013.01); *A61M 1/0064* (2013.01); *A61M 3/02* (2013.01); *A61M 3/0258* (2013.01); *A61M 3/0283* (2013.01); *A61B 2017/246* (2013.01);
(Continued)

(58) Field of Classification Search
CPC ............ A61B 17/24; A61B 2017/246; A61M 1/0058; A61M 1/0062; A61M 1/0064; A61M 1/0084; A61M 2205/3331; A61M 2205/3337; A61M 2205/82;
(Continued)

(56) References Cited

U.S. PATENT DOCUMENTS 1,603,758 A   10/1926   Fisher
1,856,811 A   5/1932    Inaki et al.
(Continued)

FOREIGN PATENT DOCUMENTS

WO   WO 2006/051206   5/2006
WO   WO 2008/058160   5/2008
WO   WO 2010/126586   11/2010

OTHER PUBLICATIONS

Nilars, Mikkel S., "Nozzle technology and Atomizer design," Hardi International A/S, 10 pages.
(Continued)

*Primary Examiner* — Imani N Hayman
(74) *Attorney, Agent, or Firm* — Levin Bagade Han LLP

(57) ABSTRACT

An irrigation and aspiration system is disclosed. The system can be configured to aspirate and irrigate alone, sequentially or concurrently. The system can be configured to aspirate and irrigate the nasal cavity. The system can be manually controlled. The system can have removable and easily cleanable reservoirs for aspirant and irrigant.

20 Claims, 34 Drawing Sheets

Related U.S. Application Data continuation of application No. 14/622,507, filed on Feb. 13, 2015, now Pat. No. 9,750,856, which is a continuation of application No. 13/080,093, filed on Apr. 5, 2011, now Pat. No. 8,956,324, which is a continuation of application No. 11/936,042, filed on Nov. 6, 2007, now Pat. No. 7,959,597.

(60) Provisional application No. 60/944,079, filed on Jun. 14, 2007, provisional application No. 60/857,457, filed on Nov. 6, 2006.

(52) U.S. Cl.
CPC .............. *A61M 2205/3331* (2013.01); *A61M 2205/3337* (2013.01); *A61M 2205/82* (2013.01); *A61M 2205/8206* (2013.01); *A61M 2210/0618* (2013.01)

(58) Field of Classification Search
CPC .. A61M 2205/8206; A61M 2210/0618; A61M 3/02; A61M 3/0258; A61M 3/0283
See application file for complete search history.

(56) References Cited

U.S. PATENT DOCUMENTS

| | | | |
|---|---|---|---|
| 2,511,973 A | 6/1950 | de la Sierra | |
| 2,566,806 A | 9/1951 | Miller et al. | |
| 2,890,699 A | 6/1959 | Miller | |
| 4,403,611 A | 9/1983 | Babbitt et al. | |
| 4,776,840 A | 10/1988 | Freitas et al. | |
| 5,024,653 A | 6/1991 | Kohnke | |
| 5,062,835 A | 11/1991 | Maitz et al. | |
| 5,098,418 A | 3/1992 | Maitz et al. | |
| 5,114,415 A | 5/1992 | Shedlock | |
| 5,318,548 A | 6/1994 | Filshie | |
| 5,403,276 A | 4/1995 | Schechter et al. | |
| 5,649,530 A | 7/1997 | Ballini | |
| 5,788,683 A | 8/1998 | Martin | |
| 5,800,425 A | 9/1998 | DeLeonardis | |
| 6,135,980 A | 10/2000 | Vu | |
| 6,149,622 A | 11/2000 | Marie | |
| 6,238,377 B1 | 5/2001 | Liu | |
| 6,328,718 B1 | 12/2001 | Chiang et al. | |
| 6,413,228 B1 | 7/2002 | Hung et al. | |
| 6,517,511 B2 | 2/2003 | Yao | |
| 6,520,931 B2 | 2/2003 | Suh | |
| 6,595,949 B1 | 7/2003 | Shapiro | |
| 6,635,034 B1 | 10/2003 | Cosmescu | |
| 6,675,994 B2 | 1/2004 | Yamamoto et al. | |
| 6,736,792 B1 | 5/2004 | Liu | |
| 6,893,414 B2 | 5/2005 | Goble et al. | |
| 6,907,879 B2 | 6/2005 | Drinan et al. | |
| 7,143,763 B2 | 12/2006 | Abate | |
| 7,435,252 B2 | 10/2008 | Krespi et al. | |
| 7,959,597 B2 | 6/2011 | Baker et al. | |
| 7,998,679 B2 | 8/2011 | Jacobs et al. | |
| 8,414,521 B2 | 4/2013 | Baker et al. | |
| 8,435,207 B2 | 5/2013 | Baker et al. | |
| 9,750,856 B2 | 9/2017 | Baker et al. | |
| 9,827,355 B2 | 11/2017 | Baker et al. | |
| 9,844,613 B2 | 12/2017 | Baker et al. | |
| 10,226,554 B2 | 3/2019 | Baker et al. | |
| 2003/0069549 A1 | 4/2003 | MacMahon et al. | |
| 2003/0145849 A1 | 8/2003 | Drinan et al. | |
| 2005/0107782 A1 | 5/2005 | Reschke | |
| 2005/0197645 A1 | 9/2005 | Karpowicz et al. | |
| 2006/0272650 A1 | 12/2006 | Hoogenakker et al. | |
| 2006/0276743 A1 | 12/2006 | MacMahon et al. | |
| 2008/0154183 A1 | 6/2008 | Baker et al. | |
| 2008/0221507 A1 | 9/2008 | Hoke et al. | |
| 2009/0281454 A1 | 11/2009 | Baker et al. | |
| 2009/0281483 A1 | 11/2009 | Baker et al. | |
| 2009/0281485 A1 | 11/2009 | Baker et al. | |
| 2011/0184341 A1 | 7/2011 | Baker et al. | |
| 2014/0378342 A1 | 12/2014 | Baker et al. | |
| 2015/0157773 A1 | 6/2015 | Baker et al. | |
| 2017/0281839 A1 | 10/2017 | Baker et al. | |
| 2017/0281851 A1 | 10/2017 | Baker et al. | |
| 2017/0290961 A1 | 10/2017 | Baker et al. | |

OTHER PUBLICATIONS

Wolfe, T.R. et al, "The Comparative Risks of Bacterial Contamination between a Venturi Atomizer and a Positive Displacement Atomizer," *American Journal of Rhinology*, 16:4, 1 page, abstract only, Jul. 2002, Oceanside Publications, Inc.

Scheler, Ott et al., "Fluorescent labeling of NASBA amplified tmRNA molecules for microarray applications", BMC Biotechnology, No. 1, vol. 9, May 15, 2009.

Dimov, Ivan K. et al., "Integrated microfluidic tmRNA purification and real-time NASBA device for molecular diagnostics", Lab on a chip, No. 12, vol. 8, Jun. 30, 2008.

U.S. Appl. No. 11/936,042, filed Nov. 6, 2007.
U.S. Appl. No. 13/080,093, filed Apr. 5, 2011.
U.S. Appl. No. 12/387,018, filed Apr. 27, 2009.
U.S. Appl. No. 12/387,054, filed Apr. 27, 2009.
U.S. Appl. No. 12/387,015, filed Apr. 27, 2009.
U.S. Appl. No. 12/387,047, filed Apr. 27, 2009.
U.S. Appl. No. 14/480,193, filed Sep. 8, 2014.
U.S. Appl. No. 14/622,507, filed Feb. 13, 2015.
U.S. Appl. No. 15/623,046, filed Jun. 14, 2017.
U.S. Appl. No. 15/623,287, filed Jun. 14, 2017.
U.S. Appl. No. 15/635,083, filed Jun. 27, 2017.

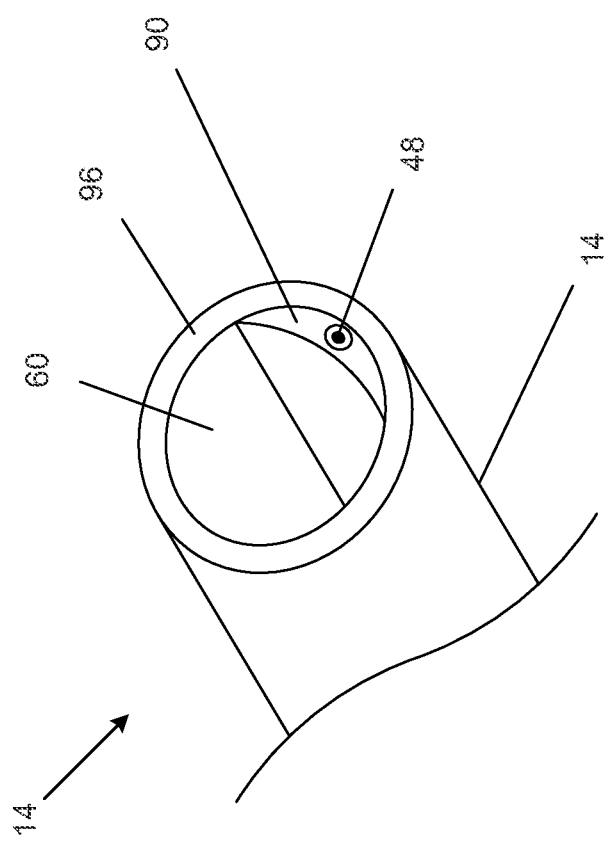

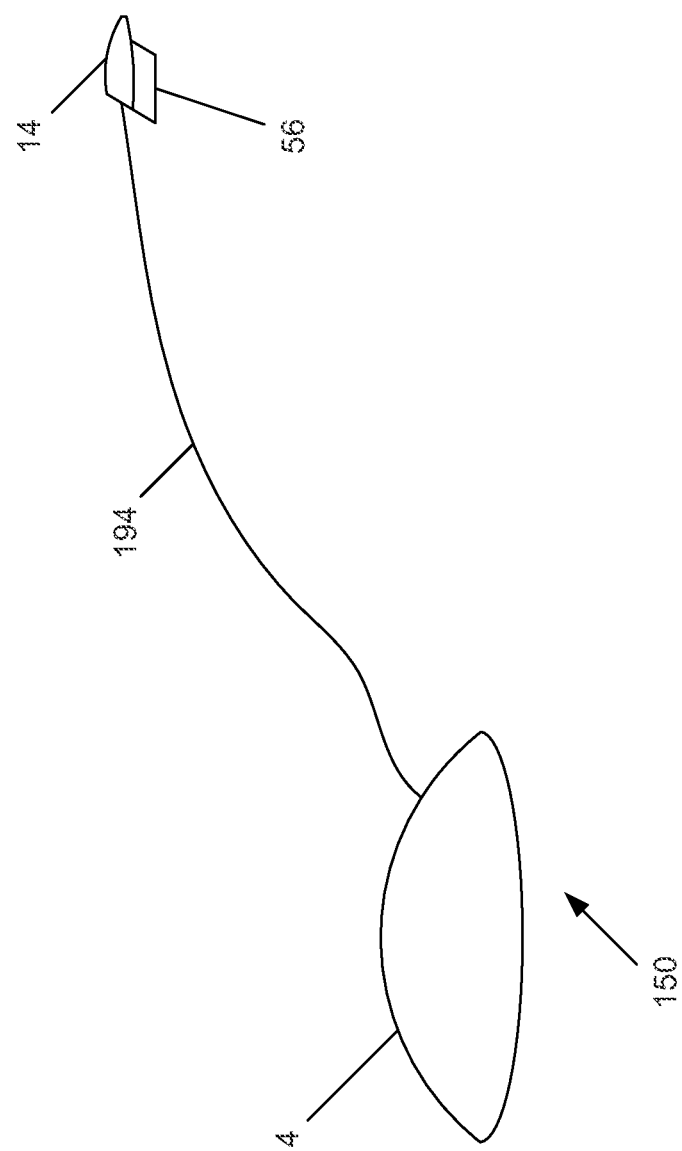

IRRIGATION AND ASPIRATION DEVICE AND METHOD

CROSS-REFERENCE TO RELATED APPLICATIONS

This application is a continuation application of U.S. patent application Ser. No. 15/623,287, filed Jun. 14, 2017, which is a continuation application of U.S. patent application Ser. No. 14/622,507, filed Feb. 13, 2015 (now U.S. Pat. No. 9,750,856, issued Sep. 5, 2017), which is a continuation application of U.S. patent application Ser. No. 13/080,093, filed Apr. 5, 2011 (now U.S. Pat. No. 8,956,324, issued Feb. 17, 2015), which is a continuation application of U.S. patent application Ser. No. 11/936,042, filed Nov. 6, 2007 (now U.S. Pat. No. 7,959,597, issued Jun. 14, 2011), which claims priority to U.S. Provisional Application No. 60/857,457, filed Nov. 6, 2006, and U.S. Provisional Application No. 60/944,079, filed Jun. 14, 2007, all of which are incorporated by reference herein in their entireties.

BACKGROUND OF THE INVENTION

1. Field of the Invention

The present invention relates to the field of medicine, specifically nasal aspiration and irrigation, as administered in the hospital as well as in the home. In particular, the device may be able to aspirate and irrigate simultaneously through one nozzle. Both actions can be controlled by one dual-function switch.

2. Description of Related Art

Nasal congestion is a ubiquitous problem in children and adults. Viral illnesses and environmental allergies in about 100 million Americans per year cause myriad symptoms including rhinitis (i.e., nasal inflammation), which causes congestion, rhinnorhea, and sinus blockage. This can cause sinusitis, but more commonly, irritation, pain, and nasal cavity blockage, which causes poor sleeping and feeding in infants and general discomfort and malaise in adults. Medical treatments are available, but inherently have side effects and financial costs. Relief of congestion can be met by blowing the nose, which is eventually irritating to the adult and difficult or impossible for a child or infant.

It has been shown that nasal suctioning, following saline irrigation, is an effective way of relieving symptoms and signs of rhinitis. Nasal suctioning can circumvent the side effects of medicines and irritation—or impossibility—of nose blowing. Manual aspirators have long been used in infants for this. However, they do not offer strong enough vacuum nor adequate evacuation time. As a result, they are variably efficacious and can be awkward and frustrating to use. Typical sinus irrigators designed for adults with sinusitis do not circumvent the problem of painful evacuation or blowing.

Furthermore, nasal congestion from viral respiratory infections causes difficulties with sleeping and eating in infants as they are obligate nose breathers. This leads to poor nutrition and restlessness which disrupts both the child's well being and the family's functioning. Worse, unresolved nasal congestion as part of an infant's viral syndrome can lead to emergency department visits or hospitalization for supplemental oxygen, frequent suctioning, and parenteral nutrition.

Several strategies are used to resolve nasal congestion. Several studies have demonstrated futility of cold medications in relieving symptoms, and most parents learn that nasal irrigation and suctioning is the best option. Routine nasal irrigation improves symptoms in adults with chronic rhinosinusitis as well as children with allergic rhinitis. Additionally, several studies have shown that saline irrigation improves nasal ciliary motility. It is thought that the saline draws fluid from the submucosal and adventitial space decreasing airway edema and softening the mucus, allowing easier suctioning. Additionally, the saline is thought to stimulate channels in the cell membrane which improves the cell's function.

Such a combination of saline irrigation and suctioning has proven benefits, especially for infants with bronchiolitis. Most studies evaluating nasal suctioning used hospital's central "wall" suction and some studies even used deep nasopharyngeal suctioning, both of which are not routinely available for home use. The studies demonstrated that appropriate suctioning reduces the need for further interventions, such as nebulizations, oxygen supplementation and admissions.

In contrast to hospital wall suction, manual nasal aspirators are available for home use. Their maximal negative pressure and flow rates are low, requiring repeated movements to and from the nose. Both parameters contribute to their imperfect quality: more pressure has been shown to be optimal (80-100 mmHg) and the short duration of their action requires repeated attempts back and forth, rendering them awkward.

Typical bulb suction syringes offer some suction, but brief and inadequate pressures can limit its utility. Additionally, the narrow and long stem allow for the possibility of mucosal damage as well as an inadequate seal at the nares. Some manual aspirators have circumvented that problem by developing better nasal tips that have improved seal and safety.

An existing manual device can sequentially (not simultaneously) deliver an agent followed by aspiration of the agent and orifice contents. It allows for neither the simultaneous activation of both functions nor the higher vacuum/flow as with a motorized device.

Still other devices have dual actions, though not designed for nasal cavities and not all-contained. For example, a hand-piece exists for surgical aspiration and irrigation. It is for surgical purposes (celioscopy) and not a home device. It requires outside sources of both vacuum and irrigant and can only perform one action at a time.

Another device describes a system for irrigating and aspirating surgical wounds. It consists of an elongate flexible suction and irrigation tip as opposed to our nozzle head configuration. The flexible shaft has a suction lumen next to or inside an irrigation lumen. The trigger controls only the irrigation mechanism while an outside source provides constant, and not intermittent, suction.

U.S. Pat. No. 4,776,840 is a hand-held evacuator and irrigation device also for surgical purposes only. Its sources of vacuum and irrigant are also outside the housing, and needs two buttons to operate the two functions. The two functions are also delivered by two different ports, not one.

U.S. Pat. No. 5,649,530 discloses a nasal cleaning device that had an atomizing chamber within the nozzle and a chamber for collecting aspirant proximal to the chamber. The aspirant and irrigant can mix together within the nozzle. This can result in unsanitary irrigant delivered to the nose.

Finally, U.S. Pat. No. 6,893,414 is an integrated infusion aspirator device also used for surgical procedures specifically addressing post-surgical pain by cleaning out surgical wounds. It allows for concurrent irrigation and aspiration of wound sites for any internal body wound. It also relies on outside sources of vacuum and irrigant.

SUMMARY OF THE INVENTION

A self-contained motorized device that offers a continuous or intermittent suction as well as a continuous or intermittent on-demand irrigant delivery to the nasal passages is disclosed. The suction and the irrigant deliver can both be out of the same nozzle. The suction and irrigation can be actuated by an ergonomically designed dual function switch. The device can have a removable irrigant and/or suction module.

A device for irrigating and aspirating biological tissue and/or secretions is disclosed. The device has a body, a nozzle articulatably connected to the body, an electronically driven fluid control system, and a manual control. The manual control can be configured to control the fluid control system. The fluid control system can be contained in the body. The fluid control system can be configured to irrigate at an irrigation pressure and aspirate at an aspiration pressure The device can also have a head articulatably connected to the body. The nozzle can be on the head. The head can be attached to the body. The fluid control system can be configured to simultaneously irrigate and aspirate. The fluid control system can be configured to vary the irrigation pressure at more than one non-zero pressure. The fluid control system can be configured to vary the pressure of aspiration at more than one non-zero pressure.

The manual control can control irrigation and aspiration. The manual control can be configured to be usable with a single digit (e.g., finger or thumb). The entire device can be handheld. The body can have a power source. The body can have a first motor.

The device can have a pump. The pump can have a piston, a blower, a turbine, a fan, one or more diaphragms, or bellows, or combinations thereof. The pump can be electrically powered. The pump can be a DC pump.

The fluid control system can have a first reservoir having a first reservoir volume. The first reservoir can be removably attached to the body. The first reservoir can have an irrigant. The fluid control system can have a second reservoir having a second reservoir volume. The second reservoir can be removably attached to the body. The second reservoir can have an aspirate. The second reservoir volume can be the same size as, smaller, or larger than the first reservoir volume.

The control can have a button. The button can be translatable in more than one dimension. The button can have a slide. The button can have a rocker switch. The button can have a wheel. The button can be depressible. The button can be configured to provide aspiration and irrigation control.

The device can have an aspiration conduit and an aspiration port in fluid communication with the aspiration conduit. The aspiration port can be on or in the head.

The device can have an irrigation conduit and an irrigation port in fluid communication with the irrigation conduit. The irrigation port can be on or in the head.

A method for irrigating and aspirating the nose is also disclosed. The method can include simultaneously irrigating at an irrigation pressure inside the nose with a device and aspirating at an aspiration pressure inside the nose with the device. The method can also include separately controlling the irrigation and aspiration with a button.

The separately controlling can include using a digit. The simultaneously irrigating and aspirating can include varying the irrigation pressure between non-zero irrigation pressures. The simultaneously irrigating and aspirating can include varying the aspirating pressure between non-zero aspiration pressures.

The device can have a body connected to a head, and the method can include articulating the head with respect to the body. The method can include holding the entire device in a hand.

The method can also include storing in the device a fluid to be irrigated. The method can also include storing in the device a fluid aspirated from the nose.

BRIEF DESCRIPTION OF THE DRAWINGS

FIG. 14 illustrates an end perspective view of a variation of the head.

FIG. 33 illustrates a variation of the irrigation and aspiration device.

DETAILED DESCRIPTION

Figure 1:
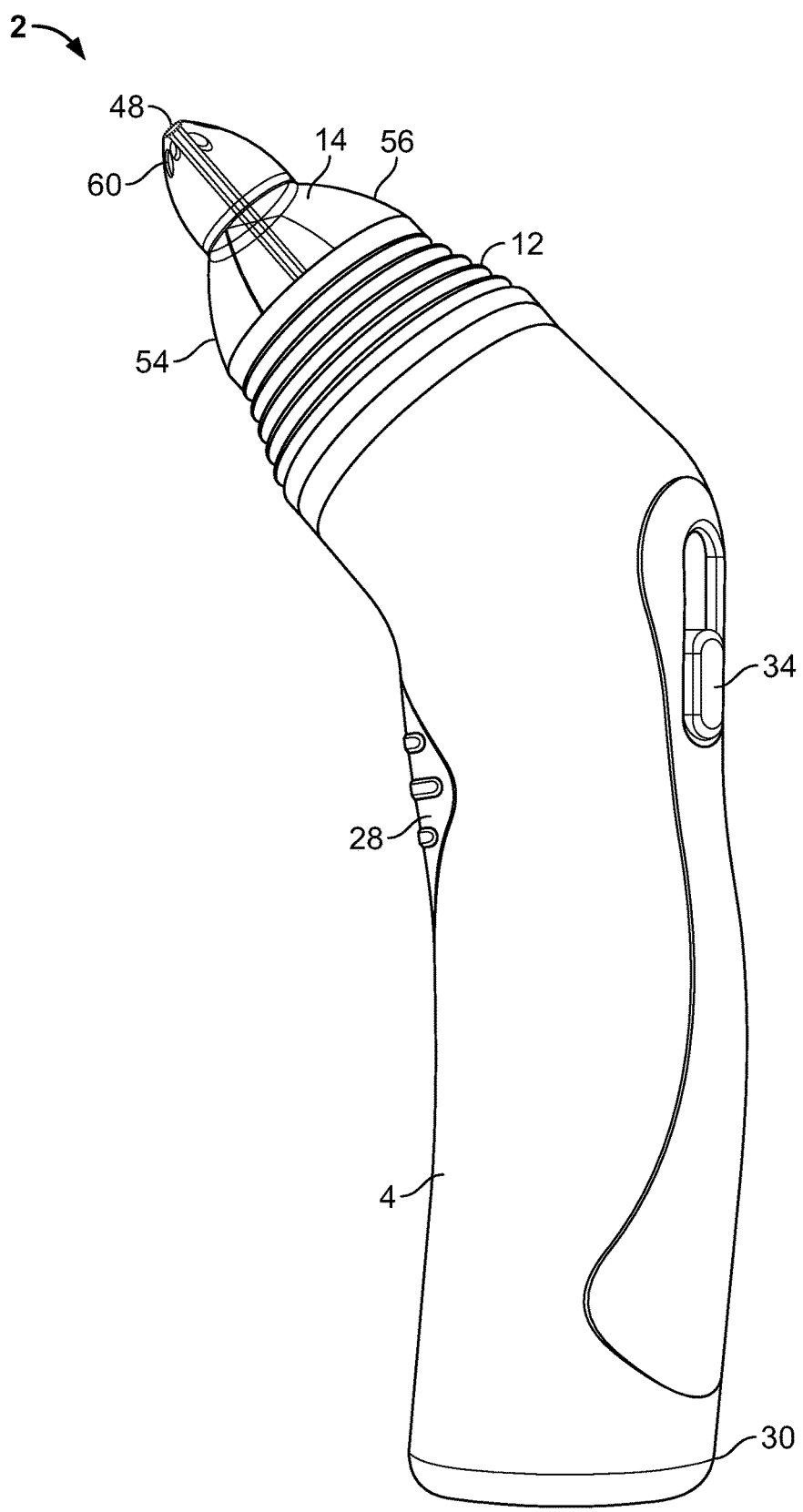
FIG. 1 illustrates a variation of the irrigation and aspiration device.
Figure 2:
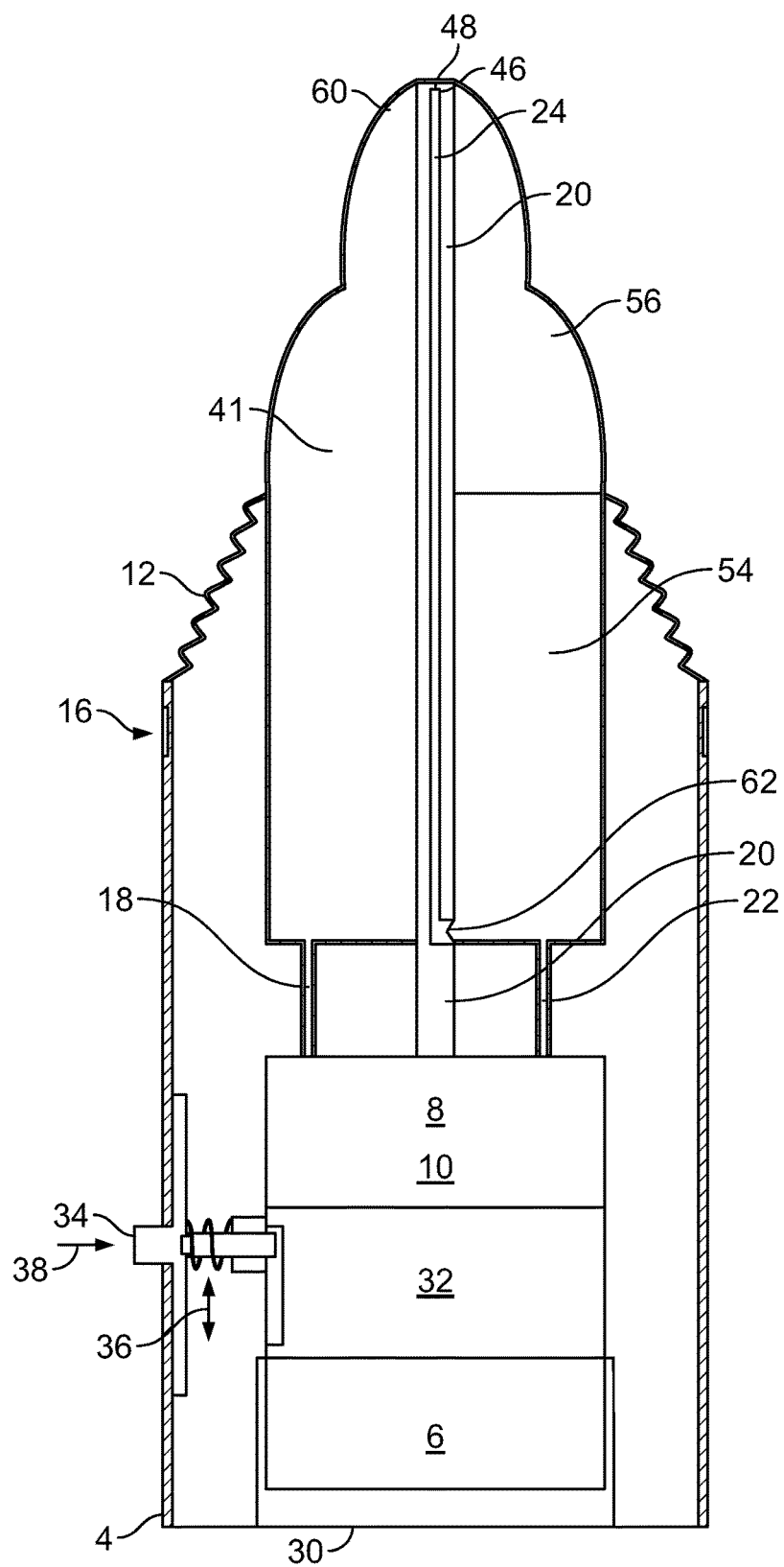
FIG. 2 is a cut-away schematic view of a variation of the of the irrigation and aspiration device.

FIGS. 1 and 2 illustrate a cleaning device 2 or system for irrigation and/or aspiration of biological tissues or fluids. The device 2 can be used in a body cavity, such as the nasal cavity, the mouth and/or throat, the ear, the eye, a skin fold, the bellybutton, a wound, or combinations thereof. The device 2 can be inserted into a natural body orifice (i.e., a normal physiological orifice, such as a nostril, mouth—including access to the throat, esophagus, stomach and lungs—ear canal, eye, naval, rectum, urethra, vagina, or adipose or fat fold), a wound, a surgical device (e.g., surgery port), or combinations thereof. The device 2 can be configured to perform nasal aspiration and/or nasal irrigation alone, sequentially or simultaneously. Aspiration can include suctioning. The device 2 can be configured to irrigate and suction concurrently. The device 2 can have an automatically driven vacuum and a manually actuated irrigation, both of which can operate simultaneously.

The device 2 can have a body 4. The body 4 can encase a power source 6 or supply. The body 4 can be connected to an external power source 6 (e.g., via a power cord). The body 4 can have a fluid control system. The fluid control system can have a driving motor. The fluid control system can have a pump 8. The pump 8 can be manual or automatic (e.g., AC or DC electrically powered). The pump 8 can be or have a piston pump, a blower, a turbine, a fan, a diaphragm pump or combinations thereof. The motor can be part of the pump 8. The fluid control system can have valves 10 that can be configured to control the flow of fluid within the fluid control system.

The outer wall as well as internal portions of the body 4 can be made from a plastic, for example ABS, polycarbonate, or a combination thereof. The outer wall as well as internal portions of the body 4 can be made by injection molding, for example by injection molding halves and assembling.

The body 4 can be attached or integral with a neck 12. The neck 12 can be attached or integral with a head 14. The neck 12 can be attached to the body 4 at a neck connector 16. The neck connector 16 can be a screw, snap, press fit connector, or combinations thereof. The neck 12 can be a flexible or rigid connection between the head 14 and the body 4.

The head 14 can be directly, or via the neck 12, attached or integral with the body 4. The head 14 can be positioned at varying angles relative to the body 4. The head 14 can articulate freely relative to the body 4 (e.g., handle). The body 4 can be held in the user's hand. The connections of the head 14 to the body 4 can be compliant and flexible so as the head 14 can pivot and translate from the perimeter of the head 14 (this is stated for exemplary purposes only, there are multiple mechanical solutions).

The neck 12 can be articulatable (e.g., pivotable, otherwise rotatable, translatable). The neck 12 can be freely articulatable, can articulate at fixed, stepped angles, or combinations thereof. For example, the neck 12 can have gussets or ribs configured to allow the head 14 to rotate with respect to the body 4.

The components within the neck 12 can be configured to rotate with the neck 12. For example, as shown in FIG. 2, an aspirant pressure line 18, atomizing channel 20 (or atomization channel), and irrigant pressure line 22 can be flexible and extendable. The irrigant channel 24 (e.g., at the irrigant pressure line 22), atomization channel 20, and aspirant channel 26 (e.g., at the aspirant pressure line 18) can each have a re-attachable division or split therein. The re-attachable division can connect in a male-female manner, such as a screw fit, snap fit, press fit, or combinations thereof. The re-attachable division can, for example, enable the head 14 to be removed from the body 4 while removing part of the channels with the head 14 and while leaving the remaining portion of the channels attached to or integral with the body 4. The re-attachable division or split can also enable rotation and translation along the channels between the head 14 and the body 4.

The body 4 can have, grip pads 28. The grip pads 28 can have soft rubber. The grip pads 28 can be attached and/or integral with the body 4. The grip pads 28 can be ergonomically located about the body 4. The grip pads 28 can be configured to be located at all or some of the locations where the user (e.g., the user's palm) naturally applies pressure to the body 4 during use.

The body 4 can have various colors, transparent, translucent, and/or opaque materials, and/or lights, for example for operational purposes and/or for entertainment of the user.

The device 2 can have a power source 6. The power source 6 can be stored completely or partially in a compartment, for example a battery compartment. The battery compartment can be in the body 4. The power source 6 can have one or more electrical cells (e.g., one or more batteries). The power source 6 can have, for example, four AA alkaline batteries in series. The power source 6 can produce 6 volts and approximately 2,000 mAh. The power source 6 can connect to an external supply of electricity (e.g., a 120 V electrical wall outlet). The battery compartment can be accessible from outside of the body 4 through a battery compartment door 30. The battery compartment door 30 can be removably attached to the body 4. The battery compartment door 30 can be hingedly attached to the body 4.

The body 4 can have a power light (e.g., LED).

The one or more pumps 8 and valves 10 can be in fluid communication with an aspirant pressure line 18, and/or an atomizing channel 20 and/or an irrigant pressure line 22. The control 32 can be configured to manage which valves 10 are open and closed, and/or how open and closed the valves 10 are, and/or what pumps 8 are on or off, and/or at what speed (e.g., flow rate and/or pressure) which pumps 8 operate. The pumps 8 and valves 10 can create positive and/or negative pressures in the aspirant pressure line 18, and/or atomizing channel 20, and/or irrigant pressure line 22. The aspirant pressure line 18, and/or atomizing channel 20, and/or irrigant pressure line 22 can have individual inflow and outflow sub-channels into the pumps 8 and valves 10.

The device 2 can have a control 32. The control 32 can be configured to provide multiple functions. The control 32 can enable user-induced, automated actuation of the device 2. For example, the control 32 can have a dual function switch, or one or more multiple-function switches, or one or more single-function switches, or combinations thereof. The switch can have a button 34. The switch can be attached or integral with the body 4, head 14, neck 12, or combinations thereof.

The control 32 can transmit power from the power source 6 to the pumps 8 and valves 10. The control 32 can be configured to receive input from the one or more switches (e.g., the button 34). The control 32 can control power delivery (e.g., electricity) from the power source 6 to the pump 8 and valves 10. The control 32 can receive a first input, for example the sliding translation of the button 34 or the pressing translation 38 of the button 34. The control 32 can receive a second input, for example the other of the sliding translation 36 of the button 34 or the pressing translation 38 of the button 34 that is not the first input. The first input can control the aspiration, for example whether aspiration is on or off and/or the intensity of the pressure and/or flow rate of aspiration. The second input can control the irrigation, for example whether irrigation is on or off and/or the intensity of the pressure and/or flow rate of the irrigation.

The switch can have a single sliding button 34. The switch can be operated by a single digit (i.e., finger 40 or thumb 42). One or more switches can control the aspiration (i.e., suction) and irrigation with one digit (i.e., finger 40 or thumb 42). The switch can be configured to receive multiple input signals (e.g., from the user). The switch can have one, two or more degrees of freedom. For example, the button 34 can receive a pressing translation 38, as shown by arrow, and a sliding translation 36, as shown by arrows. The control 32, via the multiple input signals (e.g., pressing and sliding), can be configured to separately control (e.g., binary/two-state control (on/off) and/or variable control of the magnitude of power to gradually increase or decrease) the aspiration and the irrigation. For example, one input signal (e.g., sliding) can control the aspiration and another input signal (e.g., pressing) can control the irrigation. The sliding can be along the longitudinal axis of the body 4, head 14 or neck 12. The pressing can be orthogonal to the sliding.

The switch can be bi-functional. The switch can have a rocker platform that can encase a variable speed switch. The switch can be moved from an off setting to a maximum speed (and/or on/off) setting by sliding the switch along the platform. The platform can be flush with, inside, or outside the device 2 housing. The platform can be hinged 44 at a first end and free at a second end. The platform can be resiliently pressed toward the remainder of the device 2, for example, over a balancing spring. Pressing the platform can manually actuate, or activate automatic actuation of, irrigation.

The pressing the pivoting switch housing can automatically actuate irrigation (i.e., spraying) and/or aspiration. For example, pressing the switch can trigger the control 32 to allow pressure from the pump 8 and valves 10 to be directed to the irrigation channel 24 (i.e., discharge tube) and consequently the atomization port 46 (e.g., spray nozzle), for example via the exhaust (i.e., high pressure) side of the pump 8.

The device 2 can have a first switch configured to control, for example via the pump 8 and valves 10, pressure in the aspiration channel 26. The device 2 can have a second switch configured to manually actuate a pump 8 to deliver pressure to an irrigation channel 24 and an atomization channel 20 (i.e., spray mechanism), for example schematically analogous to a squirt-gun mechanism. The first switch can be activated by a first digit 39 (e.g., the thumb 42). The second switch can be activated by a second digit 39 (e.g., the index finger 40), for example schematically and/or ergonomically analogous to a squirt-gun trigger 45.

The control 32 and/or pump 8 can be manually (e.g., user-induced) or automatically (e.g., electrically) actuated and/or powered and/or otherwise controlled. The control 32, including the switch, can be simple and intuitive to use.

The head 14 can have one or more irrigation ports 48. The irrigation ports 48 can be configured to dispense or otherwise discharge an irrigation fluid. The irrigation port 48 can be adjacent or within an atomizing port 46. The atomizing port 46 can be configured to dispense or otherwise discharge the irrigation fluid in an atomized configuration, for example, by mixing the irrigation fluid (e.g., in a liquid state) with an atomizing gas. The atomization channel 20 can have an input at an atomization reservoir 50 or from an external source (e.g., an intake port open to the outside air).

The head 14 can have a terminal end configured to be placed adjacent to, or inserted into, a biological orifice or surface to be irrigated and aspirated. For example, the terminal end of the head 14 can be configured to fit into a nostril. The terminal end of the head 14 can have a pointed conical, rounded conical, nippled, or waisted configuration or combinations thereof.

The body 4 can be configured to be ergonomically held in a single hand. The body 4 can have contours to fit the palm 52 and fingers 40 when grasped. With a filled irrigant reservoir 54 and/or aspirant reservoir 56 and in-body power source 6 (e.g., containing one or more electrical cells), the device 2 can weigh less than or equal to about 5.0 kg (11 lbs.), more narrowly less than about 2.0 kg (4.4 lbs.), for example about 0.45 kg (1.0 lbs.). The irrigant 54 and/or aspirant reservoirs 56 can be translucent and/or transparent, for example to allow a user to identify when to replace irrigant 57 and/or empty aspirant 58, and/or to check cleanliness and/or operation of the device 2.

The irrigant 54 and/or aspirant reservoirs 56 can be cleanable, for example dishwasher safe (e.g., the ability to withstand about 15 minutes at least at about 50° C., or more narrowly at least about 75° C., without substantially noticeable deformation, deterioration, or other damage, and lack of substantial deterioration or other substantial damage from similarly extended exposure to water and typical dishwasher detergents).

The head 14 can have a nozzle 59 at or near the end of the head 14. The nozzle 59 can be the tip of the head 14. The nozzle 59 can have the irrigation 48 and/or aspiration ports 60.

The aspiration channel 26 (e.g., vacuum lumen) for suctioning can connect via the aspiration port 60 (e.g., vacuum portal) of the nozzle 59 on the main housing. The aspiration channel 26 can lead to the aspirant reservoir 56 (e.g., collection chamber) for aspirant (e.g., mucous) collection.

The device 2 can have multiple, diverging aspiration channels 26, for example, to limit clogging. The aspiration channels 26 can have minimal or no tight radius curvature (e.g., the aspiration channels 26 can be substantially straight), for example to limit clogging. The aspiration channels 26 can have removably attached filters.

The aspirant reservoir 56 can be in the body 4 and/or, neck 12, and/or head 14. The aspirant reservoir 56 can be configured to receive aspirant 58 through an aspiration channel 26 and/or one or more aspiration ports 60. The aspirant reservoir 56 can be integral or fixedly or removably attached to the remainder of the device 2. The aspirant reservoir 56 can be a replaceable cartridge or ampoule. The aspirant reservoir 56 can hold aspirant 59. The aspirant 59 can include biological fluids and tissue and/or previous dispensed irrigant 57. The aspirant reservoir 56 volume can be, for example, about 5 mL.

The body 4 can have a cavity or recessed area in the housing for a removable irrigant reservoir 54. The body 4 can have an integral or attached irrigant reservoir 54.

The irrigant reservoir 54 can be in the body 4 and/or, neck 12, and/or head 14. The irrigant reservoir 54 can be configured to hold and dispense irrigant 57 through an irrigation or irrigant channel 24 and/or one or more irrigation ports 48. The irrigant reservoir 54 volume can be, for example about 5 mL.

Flow from the irrigant reservoir 54 can pass through an irrigant reservoir valve 62 before entering the irrigant channel 24 and/or irrigation port 48. The irrigant reservoir valve 62 can be a check valve (i.e., substantially or completely preventing backflow into the irrigant reservoir 54). For example, the irrigant reservoir valve 62 can be a ball valve, swing valve, clapper valve, umbrella valve, double check valve, duck bill valve, as shown, or combinations thereof.

The irrigant reservoir 54 can be integral or fixedly or removably attached to the remainder of the device 2. The irrigant reservoir 54 can hold irrigant 57. The irrigant reservoir 54 can be a replaceable cartridge or ampoule. The irrigant reservoir 54 can be disposable, replaceable, recyclable, or combinations thereof. The irrigant reservoir 54 can be pre-filled with irrigant 57 or ready for adding all or a component (e.g., water) of the irrigant 57. The irrigant reservoir 54 can be divided into multiple sub-reservoirs. For example, one sub-reservoir can have salt and another irrigant reservoir 54 can have water. The sub-reservoir contents can mix (e.g., creating saline solution) when the irrigant is dispensed.

The irrigant reservoir 54 can be the same volume, a larger volume than, or a smaller volume than the aspirant reservoir 56. For example, the aspirant reservoir 56 volume can be about 100 or less times larger than the irrigant reservoir 54 volume, or more narrowly, about 20 or less times larger than the irrigant reservoir 54 volume, or more narrowly, about 7 or less times larger than the irrigant reservoir 54 volume, or more narrowly, about 3 or less times larger than the irrigant reservoir 54 volume, or more narrowly about 1.5 or less times larger than the irrigant reservoir 54 volume, for example the aspirant reservoir 56 volume can be about 1.25 times the irrigant reservoir 54 volume.

The irrigant reservoir 54 can be a first color (e.g., blue), the aspirant reservoir 56 can be the first color or a second color (e.g., yellow or red). The irrigant reservoir 54 and/or aspirant reservoir 56 can be transparent, translucent or opaque. The irrigant reservoir 54 can seat into the device 2 in a different configuration than the aspirant reservoir 56. For example, the irrigant reservoir 54, aspirant reservoir 56 and the remainder of the device 2 can be configured so as to not be able to insert the irrigant reservoir 54 in the device 2 in place of the aspirant reservoir 56 and/or vice versa.

The irrigation fluid or irrigant 57 can have or be water, saline solution, zinc solution (e.g., zinc sulfate solution), alcohol, anesthetic agent, analgesic agent, antipyretic agent, anti-inflammatory agent such as a non-steroidal anti-inflammatory agent (e.g., ibuprofen, aspirin, salicylic acid. COX02 inhibitor, COX-3 inhibitor), acetaminophen, live attenuated flu vaccine, antihistamine (e.g., azelastin hydrocholoride), corticosteroid (e.g., fluticasone propionate), topical decongestant (oxymetazoline hydrochloride), vitamin (e.g. vitamin c, ascorbic acid), nicotine, other therapeutic or diagnostic medication, or combinations thereof.

The irrigant 57 can combine with an atomizing gas at the atomizing port 46. The atomizing port 46 can be a nozzle 59 configured to atomize the irrigant 57.

The atomizing gas can have or be air carbon dioxide, oxygen, nitrogen, nitrous oxide, another anesthetic, or combinations thereof.

Figure 3:
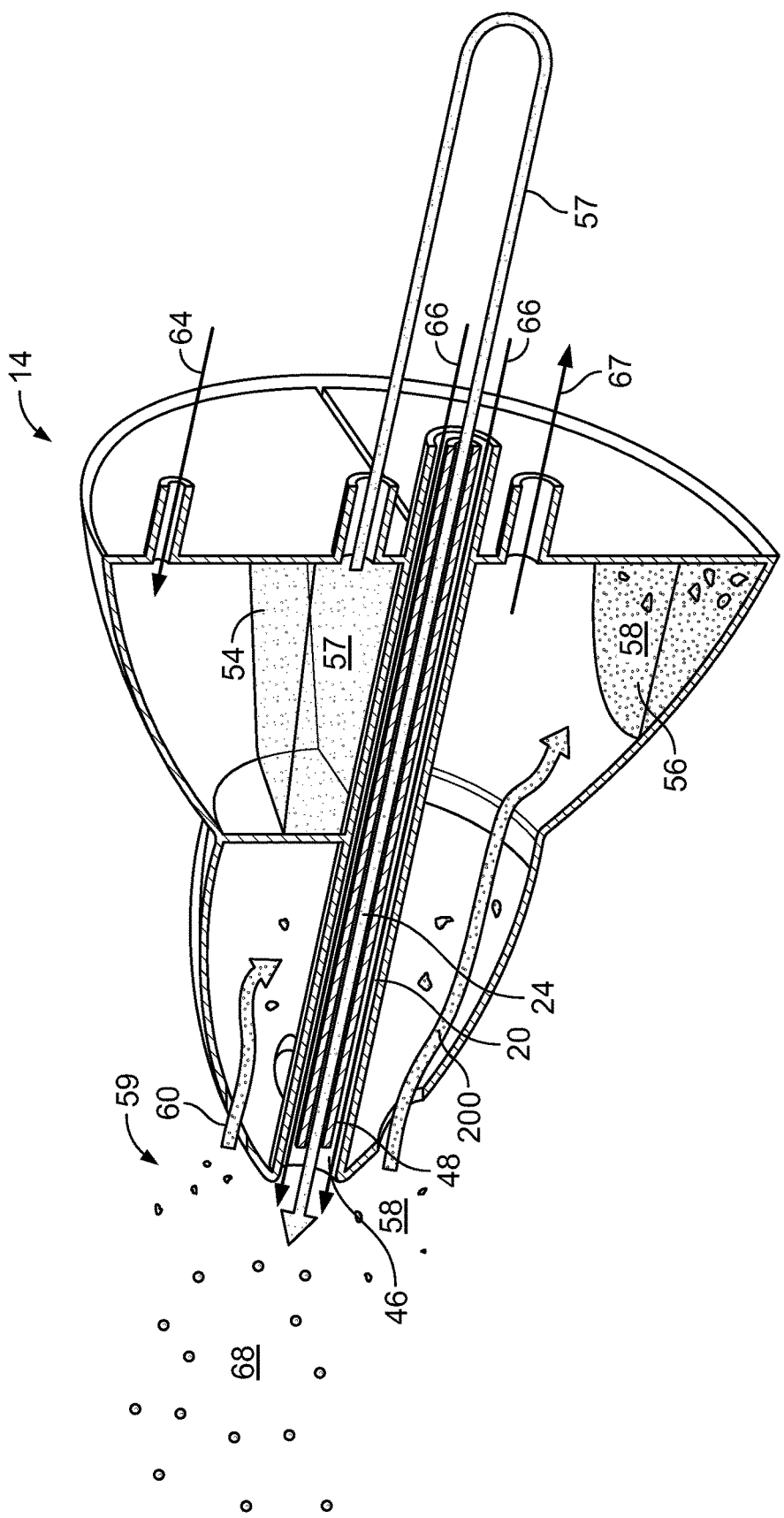
FIG. 3 is a cut-away view of a variation of the head.

FIG. 3 illustrates a variation of the head 14 with irrigant 57 and aspirant 58 flow. Irrigant pressure 64, as shown by arrow, can be applied to the irrigant reservoir 54. The irrigant pressure 64 can force the irrigant 57 from the irrigant reservoir 54 through the irrigation channel 24.

Atomizing pressure 66, as shown by arrows, can be applied to the atomizing channel 20. The atomizing pressure 66 can for the atomizing gas through the atomizing channel 20.

The nozzle 59 can be configured to mix the irrigant 57 and the atomizing gas at the atomizing port 46. The nozzle 59 can be configured to nebulize or atomize the irrigant 57 with the atomizing gas as the irrigant 57 flows out of the atomizing port 46. The atomized irrigant 68 can flow away from the nozzle 59.

The atomized irrigant 68 can include particles having a diameter from about 0.1 μm (0.004 mil) to about 100 μm (4 mil) upon exit from the atomization port 46. The atomized irrigant 68 particles can have a high mobility and can substantially uniformly coat, adhere and interact with the target site, tissues, and fluids.

The irrigant 57 can be delivered as one or more unatomized streams (i.e., shower-like) without the mixing with an atomizing gas. For example, the device can have no atomization channel 20.

The nozzle 59 can be configured to deliver the irrigant 57 in a stream or flood (e.g., not atomized), for example by having no atomization port 46 (e.g., or other atomization elements).

A negative aspirant pressure 67 can be applied to the aspirant reservoir 56. The aspirant 58 can flow, as shown by arrows, through the aspiration ports 60 and into the aspirant reservoir 56. The aspirant 58 can collect in the aspiration reservoir 56.

The irrigant port 48 and atomizing port 46 can be radially central to the terminal end of the head 14. The aspirant ports 60 can be radially off-center or otherwise away from the irrigant port 48 and atomizing port 46 on the head 14.

There is an inner lumen (irrigation lumen) of the nozzle 59 that is either central or eccentric which delivers a spray of saline upon manual/automatic actuation, much like a water gun inside of a suction device. This portion of the nozzle 59 corresponds to the aspiration portal 60 of the nozzle 59 base on the main housing.

The control 32, pumps 8, and heads 14 can be configured to provide various irrigation flow characteristics. For example, the device 2 can be configured to flood unbroken, unhollow stream, for example substantially cylindrical stream), and/or atomize, and/or conical (e.g., hollow or unhollow conical stream) irrigation characteristics. The flow characteristics can be automatically or manually adjusted. The nozzle 59 or head 14 can be manually replaced with a differently configured nozzle 59 or head 14 to change the irrigation characteristics.

Figure 5:
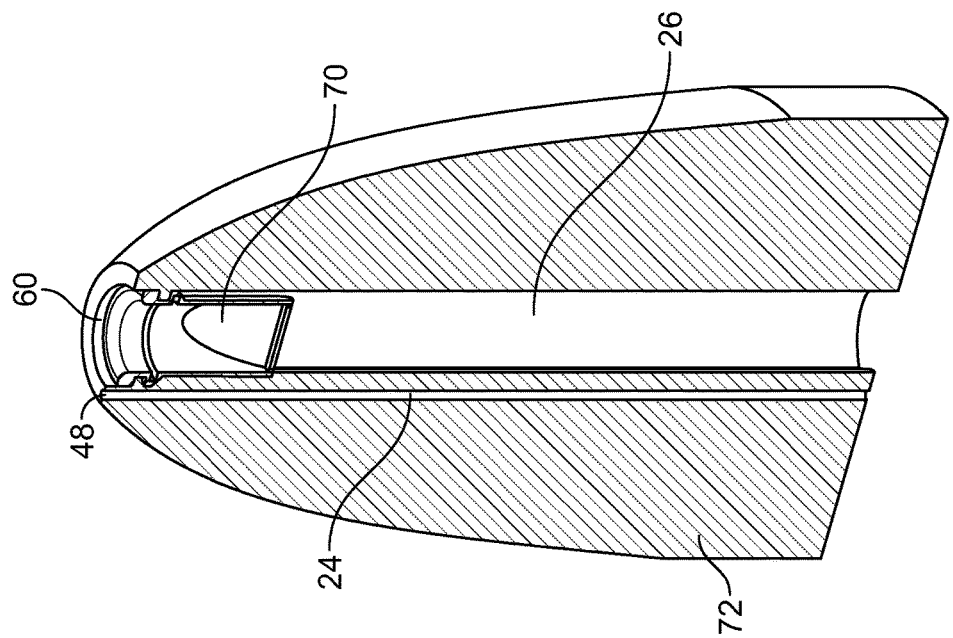
FIG. 5 is a partially see-through cut-away view of the variation of the head of FIG. 4.
Figure 4:
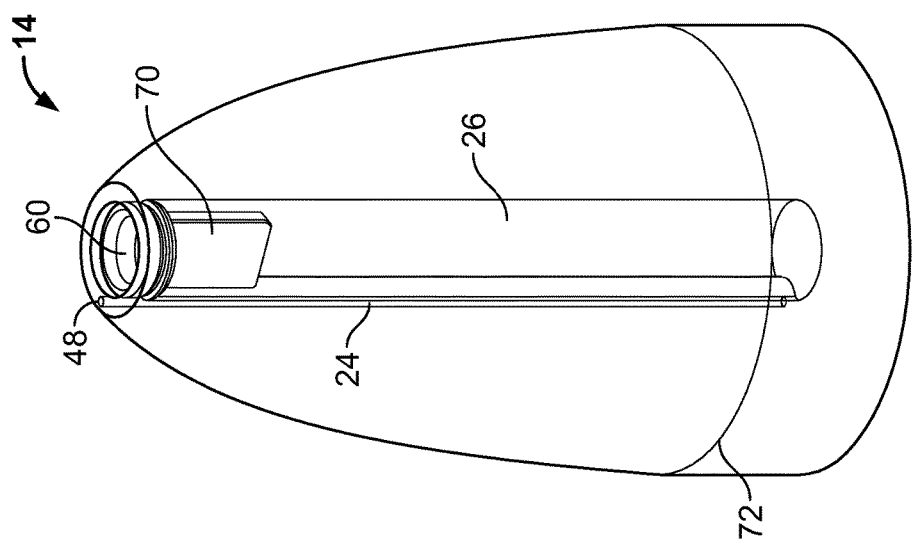
FIG. 4 is a partially see-through view of a variation of the head.

FIGS. 4 and 5 illustrate that the aspiration port 60 can have an inflow check (i.e., one-way) valve 10 for inflow configured to substantially or completely prevent backflow of aspirant 58 from the aspiration channel 26 or reservoir 56. The inflow check valve 10 can be or have a ball valve, swing valve, clapper valve, umbrella valve, double check valve, duck bill valve 70, as shown, or combinations thereof. The inflow check valve 10 can be integral or fixedly or removably attached to the aspiration port 60 and/or the aspiration channel 26 and/or the aspirant reservoir 56. The aspiration port 60 can be radially central to the terminal end of the head 14. The irrigation channel 24 can be radially off-center or otherwise away from the aspirant port 60 on the head 14.

The head 14 can have an attachment ring 72 on the inside or outside of the head 14. The attachment ring 72 can be configured to attach to the neck 12 and/or the body 4.

Figure 6:
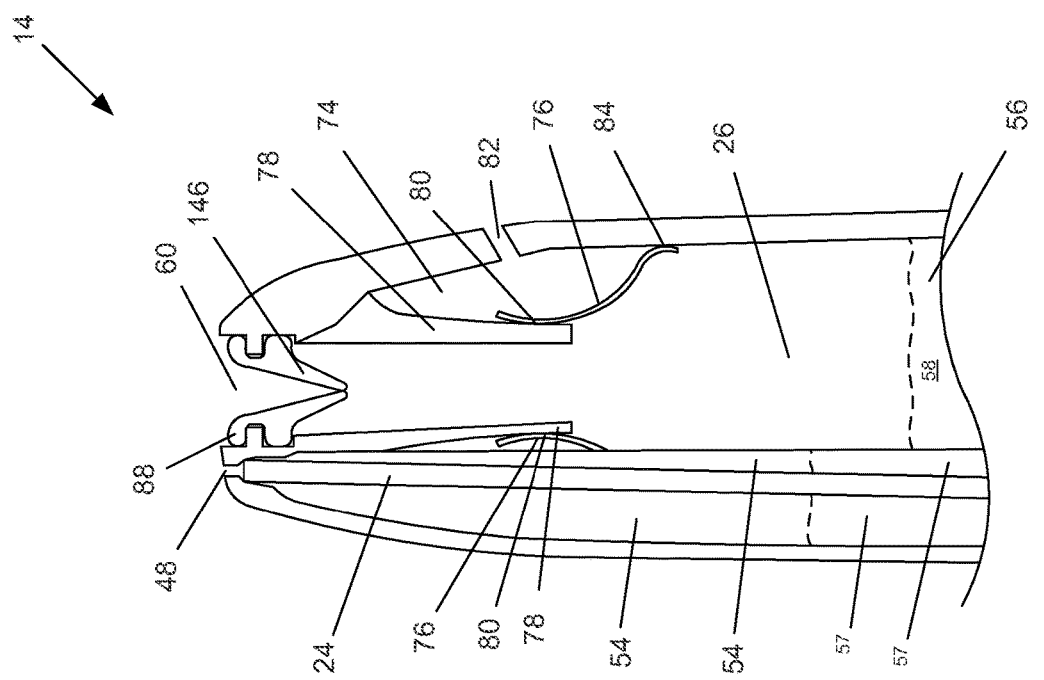
FIG. 6 is a cut-away view of a variation of the head.

FIG. 6 illustrates that the aspiration channel 26 or aspirant reservoir 56 can have a exhaust trap 74. The exhaust trap 74 can have a trap valve 76. The trap valve 76 can be a resilient flap. The trap valve 76 can be a check valve 10 configured to release excessive pressure from the aspirant reservoir 56 and/or aspirant channel 26 into the exhaust trap 74. For example, the excessive pressure in the aspirant reservoir 56 or aspiration channel 26 can force fluid (i.e., aspirant 58 or gas in the aspirant reservoir 56 or aspiration channel 26) between the trap valve 76 and a relatively rigid trap flange 78. The contact area of the trap valve 76 and the trap flange 78 can be a trap intake seal 80.

The trap flange 78, and/or aspiration channel 26 can direct incoming flow of aspirant 58 from the aspiration port 60 adjacent to the trap intake seal 80 so that a low pressure is naturally produced on the aspiration channel-side 26 and/or aspirant reservoir-side 56 of the trap intake seal 80 during aspirant 58 flow from the aspiration port 60 into the aspirant reservoir 56.

The exhaust trap 74 can drain through an exhaust trap port 82 to the outside of the device 2 or to a separate overflow exhaust reservoir (not shown). The exhaust trap port 82 can be open or can have a manual or automatic pressure release valve 10, for example a check valve 10. The device 2 can be configured to drain aspirant 58 (e.g., passively or under applied pressure) from the aspirant reservoir 56 through the exhaust trap 74 and the exhaust trap port 82.

The exhaust trap 74 can have a trap overflow seal 84. The trap overflow seal 84 can be a check valve 10 configured to release excessive pressure from the exhaust trap 74 into the aspiration channel 26 and/or aspirant reservoir 56. The trap overflow seal 84 can be made from a portion of the trap valve 76 and the outer wall of the aspiration channel 26 or aspirant reservoir 56.

The aspiration valve 86 can be integral with or attached to an aspiration valve gasket 88. The aspiration valve 86 and/or aspiration valve gasket 88 can be snap-fit (as shown, around an extending ring or collar configuration), press-fit, attached with an adhesive, or otherwise attached to the aspiration port 60.

The irrigation channel 24 can be located in the irrigant reservoir 54.

Figure 8:
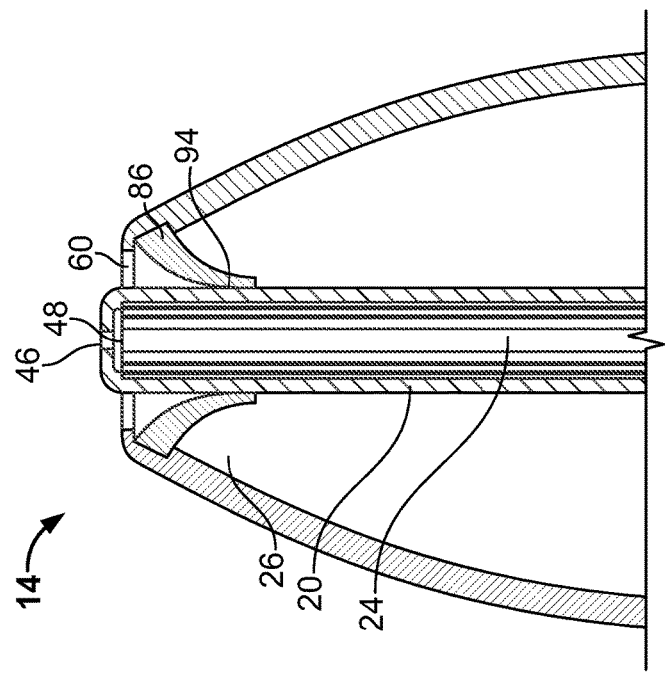
FIG. 8 is a close-up cut-away view of the variation of the head of FIG. 7.
Figure 7:
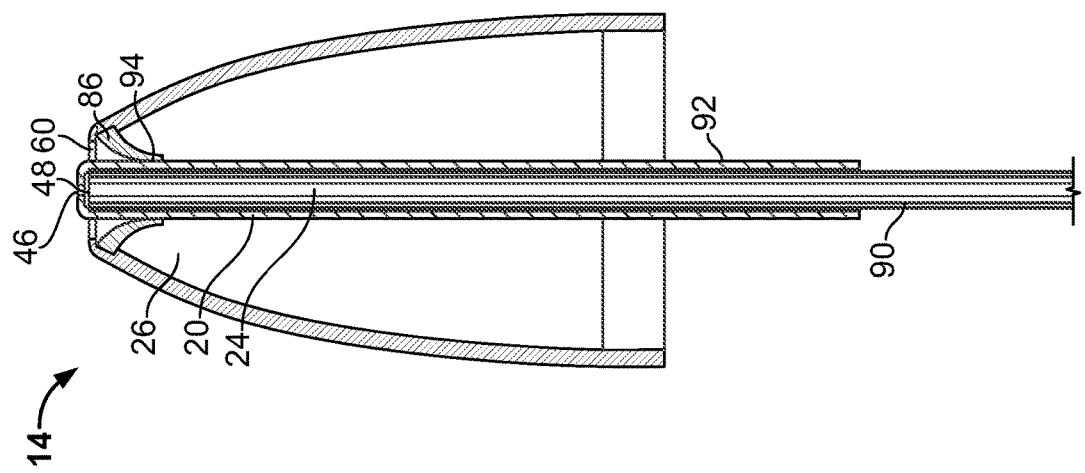
FIG. 7 is a cut-away view of a variation of the head.

FIGS. 7 and 8 illustrate that the irrigation channel 24 can be concentric with the atomizing channel 20. The irrigation channel 24 can be in an irrigation conduit 90. The atomizing channel 20 can be in an atomizing conduit 92. The irrigation conduit 90 can be concentric with the atomizing conduit 92. The irrigation channel 24 can be inside the atomizing conduit 92.

The aspiration valve 86 can be a check valve 10 concentric with the atomizing port 46 and/or irrigation port 48. The aspiration valve 86 can form the aspiration seal 94 against the aspiration 96 and/or irrigation conduit 90.

Figure 9:
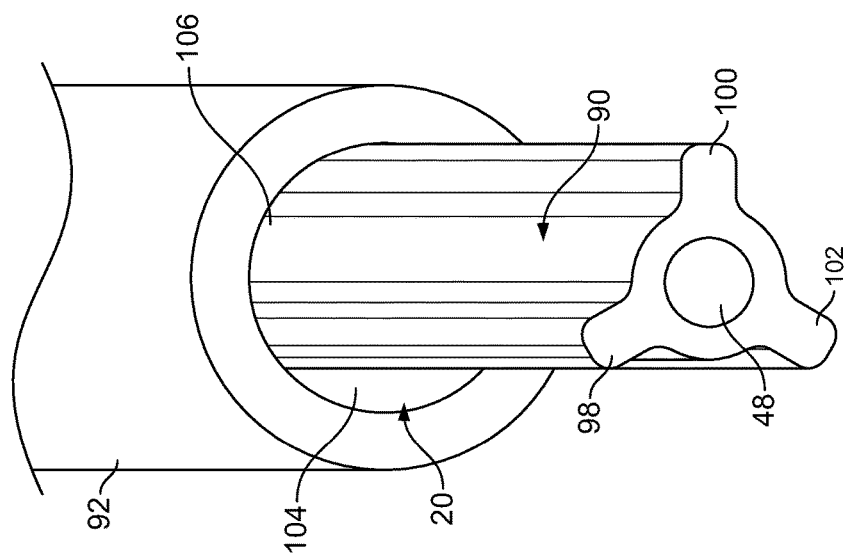
FIG. 9 is a close-up end perspective view of a variation of the irrigation and atomizing conduits.
Figure 12:
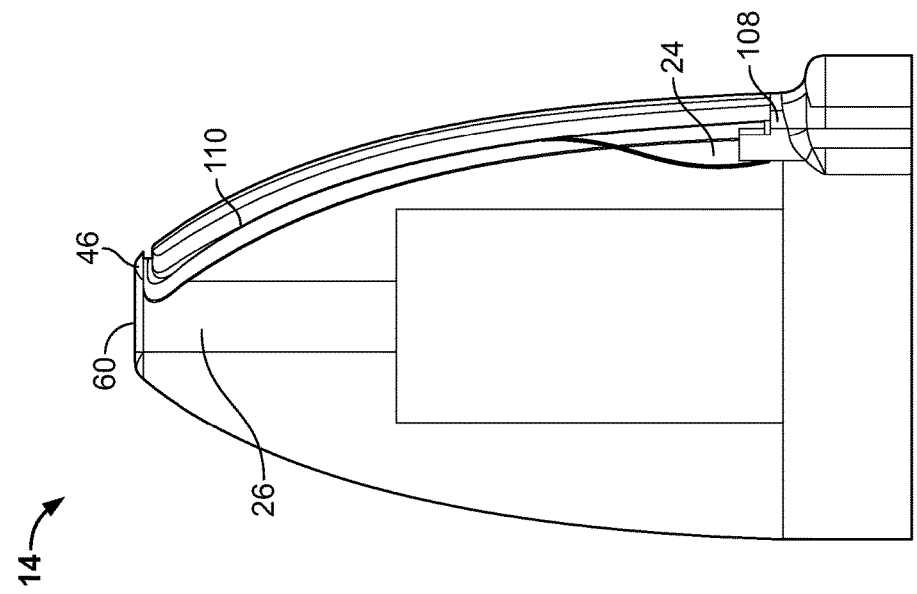
FIGS. 12 and 13 are, respectively, side and off-center front partial see-through views of the head of FIG. 10.

FIG. 9 illustrates that the irrigation conduit 90 can have first 98, second 100, third 102 and more atomizing vanes. The vanes can be configured to radially extend from the center of the irrigation conduit 90. The vanes can longitudinally extend along all or part of the irrigation conduit 90. The vanes and the atomizing conduit 92 can form first 104, second 106, third and more atomizing sub-channels within the atomizing channel 20. The atomizing sub-channels can be venturis 185. The edges of the vanes can be sharpened, for example to induce turbulent flow around the edges of the vanes.

The concentric tube design (i.e., with the irrigation channel 24 internal to a concentric aspiration channel 26 (proximal to the respective ports) can have the outer tube (e.g., atomization channel 20) be shorter than the inner tube (e.g., irrigation channel 24). The difference in length between the atomization 20 and irrigation channels 24 can allow for the irrigant 57 to be atomized when pressurized irrigant 57 passes up the center tube (e.g., irrigation channel 24) which can be filled from the reservoir, and pressurized air can pass through the outer tube (e.g., aspiration channel 26).

The concentric tube design can be inverted with respect to the configuration described supra. For example, the irrigant reservoir 54 can be inverted and the atomization channel 20 can be central to the concentric irrigation channel 24. The nozzle 59 can be "flooded" to spray the irrigant 57 by filling the outer tube (i.e., irrigant channel 24) with pressurized irrigant 57 and the inner tube (e.g., atomization channel 20) with pressurized air or other gas. For example, infants can be laying down and receive drops of irrigant 57 and toddlers can be sitting up and receive atomized irrigant 57.

Figure 10:
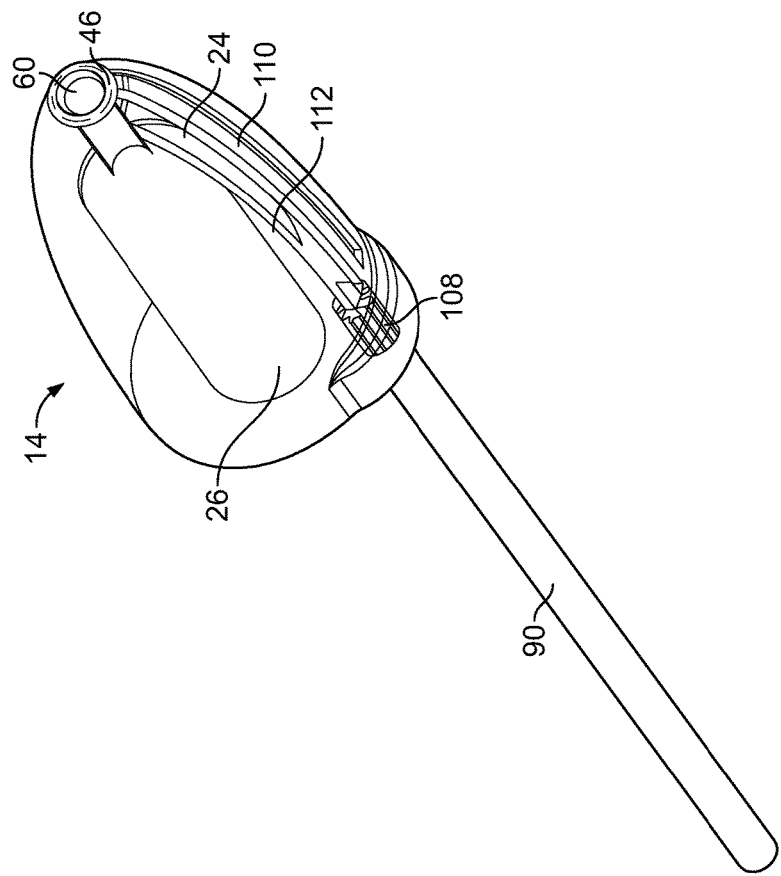
FIG. 10 is a perspective partially see-through view of a variation of the head and the irrigation conduit.
Figure 11:
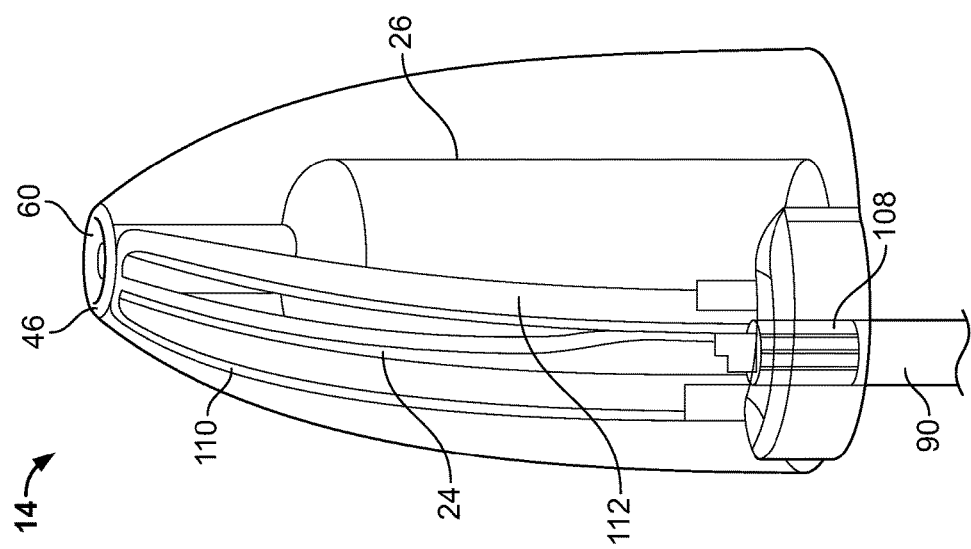
FIG. 11 is a front quarter partially see-through view of the variation of the head and the irrigation conduit of FIG. 10.

FIGS. 10 and 11 illustrate that the irrigation conduit 90 can be integral with or attached to the head 14. The head 14 can have an irrigation conduit port 108. The irrigation conduit port 108 can receive the irrigation conduit 90.

FIGS. 10 through 13 illustrate that the head 14 can have first 110, second 112 and more atomizing channels 20. The atomizing channels 20 can be on the outer surface of the head 14. The atomizing channels 20 can have venturis 185.

The irrigation channel 24 in the head 14 can extend from the irrigation conduit port 108 to the irrigation port 48 (not shown, but can be located inside the head 14 and adjacent to or in the atomizing port 46). The first and second aspiration channels 26 can merge. The first and second aspiration channels 26 can merge adjacent to the irrigation port 48. The first and second aspiration channels 26 can merge adjacent to the aspiration port 60.

The atomization gas can flow from outside the head 14, for example from outside the device 2 or from an atomization conduit 92 within, attached, or adjacent to the irrigation conduit 90.

FIG. 14 illustrates that the irrigation port 48 can be located adjacent to the aspiration port 60. The irrigation port 48 can be completely or partially surrounded by the aspiration port 60. The aspiration port 60 can be completely or partially surrounded by the irrigation port 48. The irrigation conduit 90 can be inside the aspiration conduit 96. The irrigation conduit 90 can be non-concentric with the aspiration conduit 96. The irrigation port 48 can be flush on one side of the aspiration conduit 96.

Figure 16:
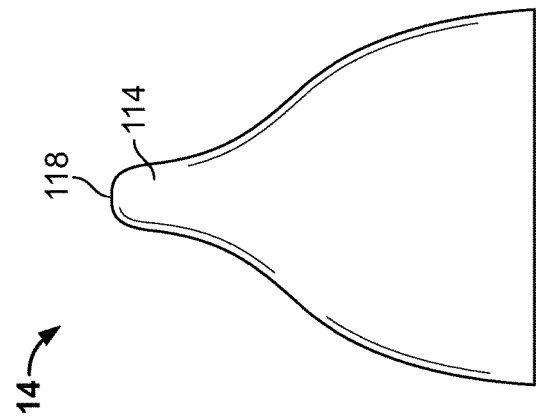
FIGS. 15 and 16 illustrate variations of the head.
Figure 15:
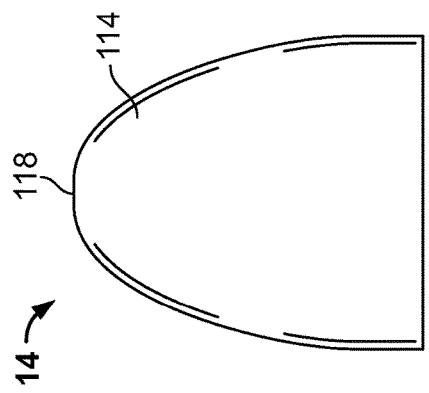
Figure 13:
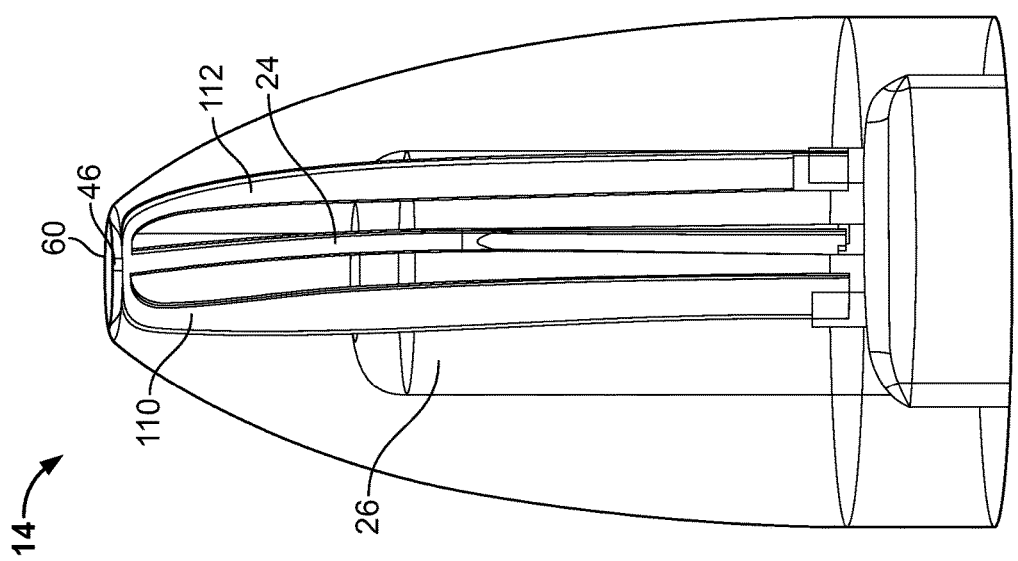

FIG. 15 illustrates that the head 14 can have one or more ports (representing the irrigation 48 and/or aspiration 60 and/or atomization ports 46). The head 14 can be configured as a bulb 114. Non-skewed alignment along a longitudinal axis of the head 14 presents a secondary challenge to the user and/or patient. FIG. 16 illustrates that the terminal end of the head 14 can be configured as a nipple 116. The terminal end of the head 14 can be bulged or waisted. The terminal end of the head 14 can have a larger radius distal to the port 118, for example, to prevent overinsertion of the head 14 into a natural body orifice.

The terminal end of the head 14 can be configured to make a positive seal with the irrigation and aspiration site (e.g., the nostril). The head 14 can seal to the irrigation and aspiration site analogous to a ball and socket joint and/or similar to nested tubes. The terminal end of the head 14 can be rotationally symmetric about a longitudinal axis of the head 14. The rotational alignment can be decoupled from the sealing functionality, for example allowing one more degree of freedom for the user.

The terminal end of the head 14, or all of the head 14, can be made from and/or covered or coated with, a compliant material such as silicone rubber or foam. The terminal end of the head 14 or all of the head 14 can be compliant, for example, to permit sealing to differently-shaped nostrils. The terminal end of the head 14, or all of the head 14 can be sufficiently rigid to not deform against the negative pressure of the aspiration.

Figure 17:
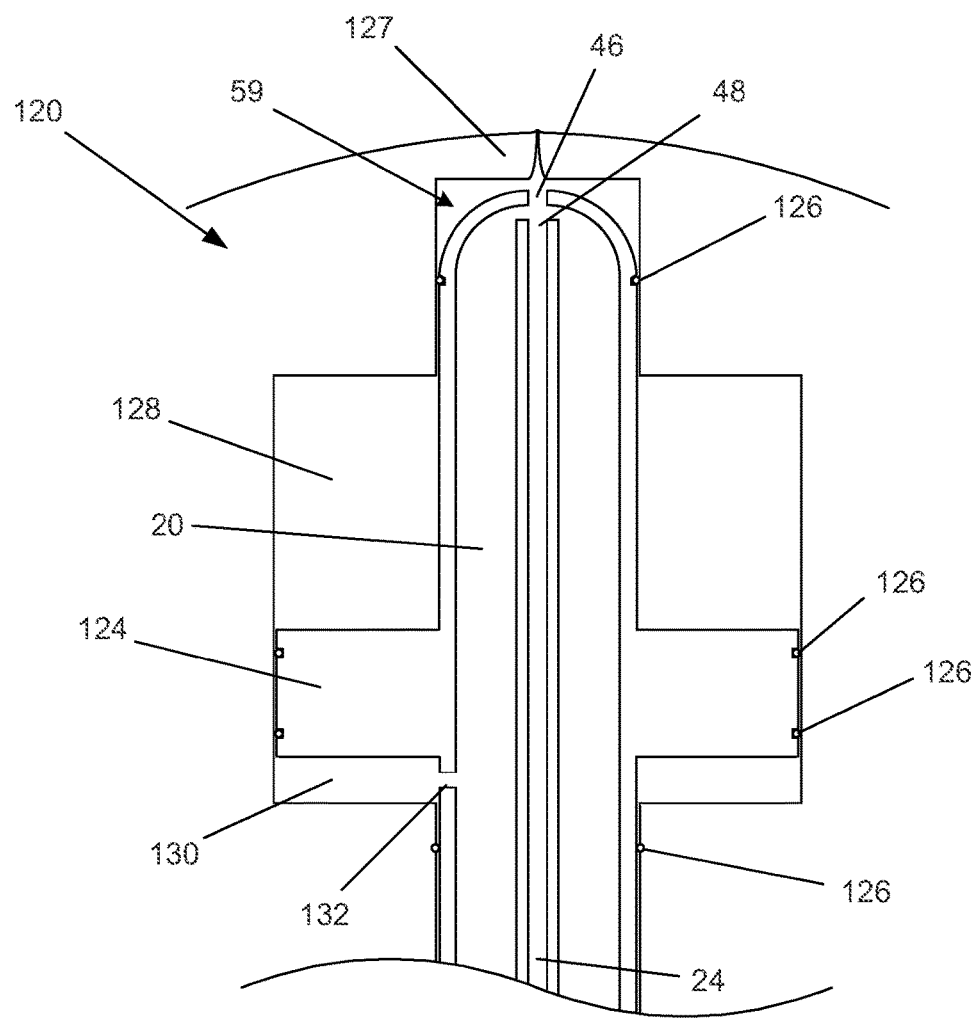
FIGS. 17 and 18 are cut-away views of a variation of the head in first and second configurations, respectively.

The head 14 can have an irrigation component 120 and an aspiration component 122. FIG. 17 illustrates that the irrigation component 120 can have a piston 124 within a cylinder. The piston 124 can have one or more gaskets 126. The gaskets 126 can fluidly seal between the piston 124 and the cylinder. The piston 124 can have a nozzle 59 at a terminal end of the piston 124. The piston 124 can be integral with or attached to the atomizing channel 20 and the irrigant channel 24.

The irrigation component 120 can have a resilient valve 10 or seal, for example an elastomeric seal 127. The elastomeric seal 127 can fluidly separate the nozzle 59 from the outside of the head 14 (e.g., during use, the nasal cavity, for example), for example when the device 2 is in a retracted (e.g., not irrigating) configuration.

The cylinder can be volumetrically rigid or compliant (e.g., if desired to expand to accommodate excessive pressures). The cylinder can have a cylinder top 128 and a cylinder bottom 130. The cylinder top 128 can be the volume fluid sealed by the piston 124 from the volume of the cylinder bottom 130. The atomizing channel 20 can have one or more cylinder ports 132 into the cylinder top 128 and/or cylinder bottom 130. The cylinder port 132 can have an active or passive valve 10.

Figure 18:
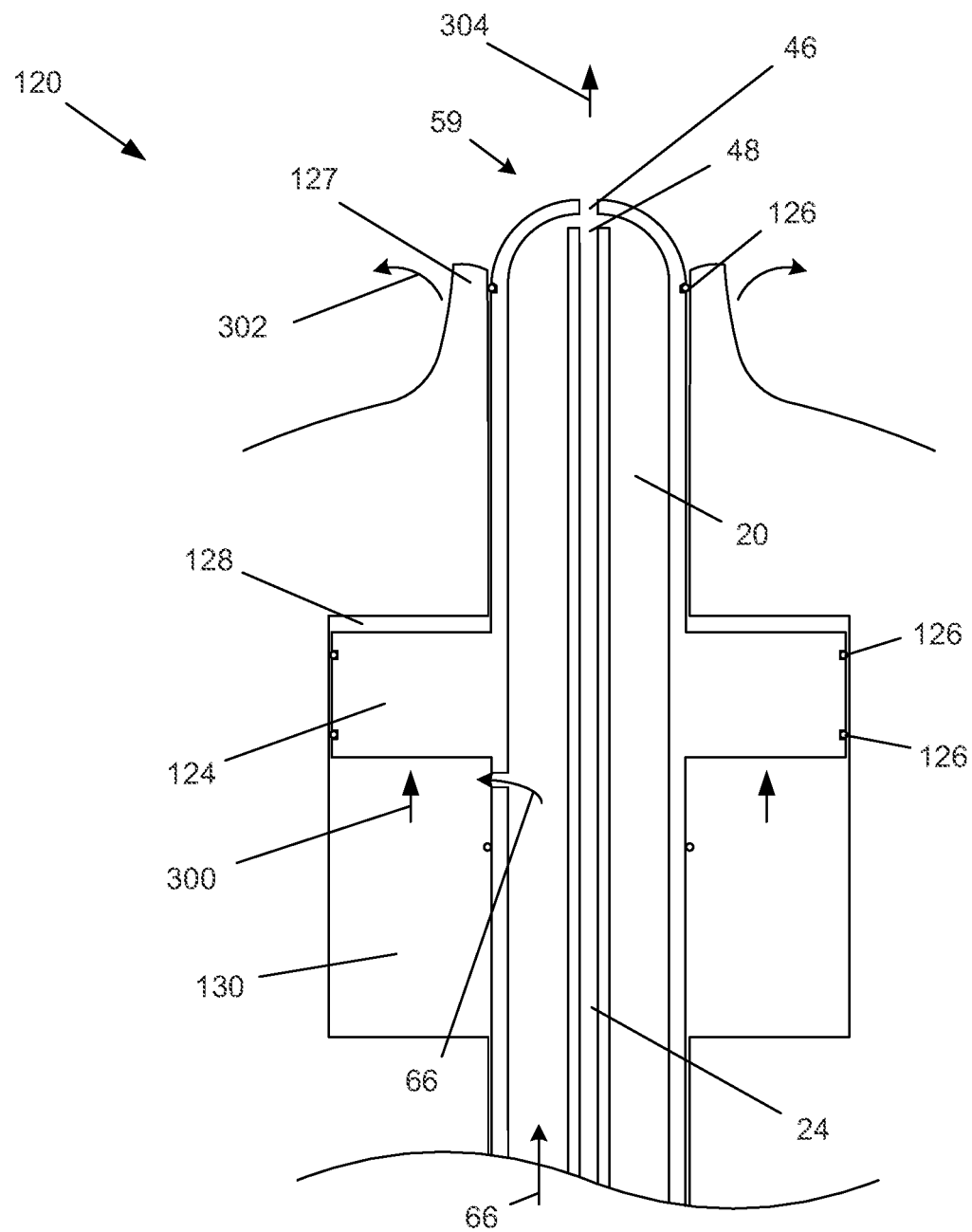

FIG. 18 illustrates that high pressure fluid (e.g., atomizing gas) can be introduced under an atomizing pressure 66, as shown by arrows, into the atomizing channel 20. The atomizing pressure 66 can enter the cylinder bottom 130 or top 128 (for exemplary purposes, shown as cylinder bottom 130). Force from the atomizing pressure 66 and/or another force (e.g., from a motor not shown) can translate, as shown by arrows 300, the piston 124 toward the elastomeric seal 127.

The nozzle 59 can be translated toward and out the elastomeric seal 127. The translation of the nozzle 59 can cause the seal 126 to rotate open, as shown by arrows 302. The rotated open elastomeric seal 127 can fluidly seal against the nozzle 59, for example directly or via one or more gaskets 126.

The atomization port 46 can translate out of the elastomeric seal 127, as shown by arrow 304. The irrigant 57 can be delivered via the irrigation port 48, for example with the flow exiting the atomizing port 46 unobstructed by the elastomeric seal 127.

Instead of, or in combination with, a piston-deployed irrigation component 120, the device 2 can have a reciprocating and/or syringe-deployed irrigation component 120, similar to the piston-deployed irrigation component 120 shown in FIGS. 17 and 18.

Figure 19:
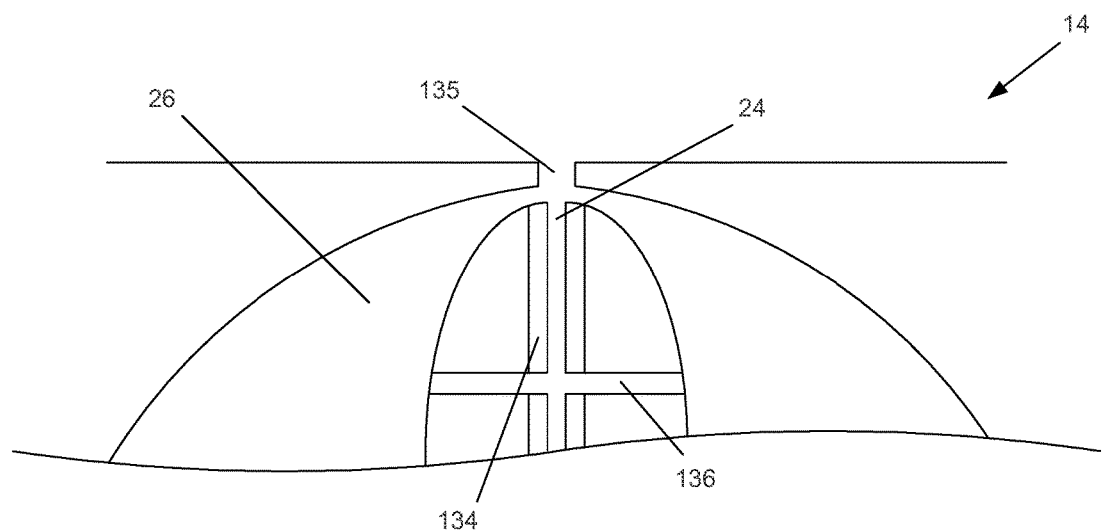
FIG. 19 is a cut-away view of a variation of the head.

FIG. 19 illustrates that the head 14 can have a single combined port 135 for aspiration and irrigation. The aspiration can occur concurrently or subsequent to the irrigation. The aspiration channel 26 can be configured to direct the suction pressure of the aspiration adjacent to the perimeter of the combined port 135. The irrigation channel 24 can be configured to direct the irrigation to the center of the combined port 135.

The irrigation channel 24 can have an irrigation channel lining 134. The irrigation channel lining 134 can actively (e.g., can be movable, such as an electro-active polymer skin) or passively (e.g., by the shape of the channel lining 134) focus the exiting stream of irrigant 57. The irrigation channel lining 134 can form a venturi 185 in the irrigation channel 24. The irrigation channel lining 134 can be integral with, or fixedly or removably attached to the irrigation channel 24.

The irrigation channel 24 can have an irrigation channel break 136. The irrigation channel break 136 can be configured to act as a venturi 185. The irrigation channel break 136 can be configured to increase turbulence in the flow of the irrigant 57 through the irrigation channel 24.

Figure 20:
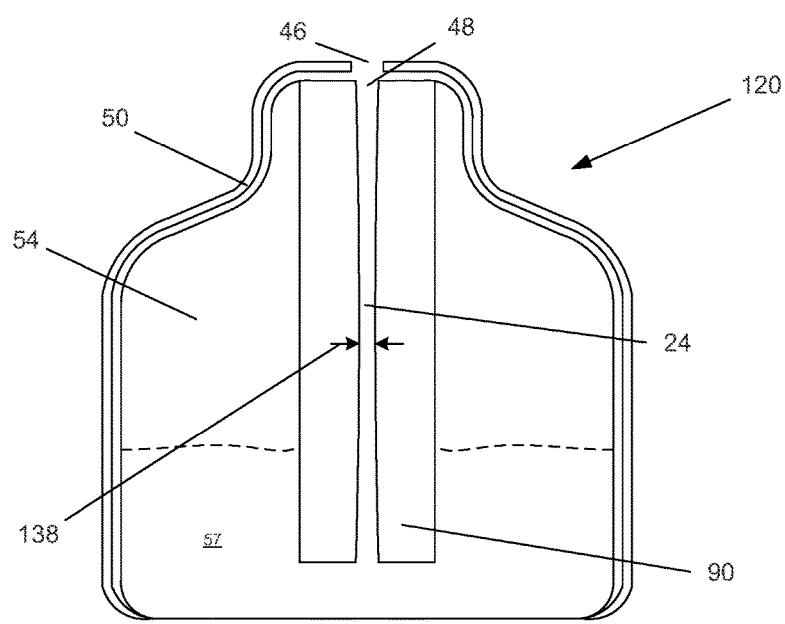
FIG. 20 is a cut-away view of a variation of the irrigation and aspiration device.

FIG. 20 illustrates that the irrigation component 120 can have an atomizing reservoir 50 or atomizing channel 20 (labeled as a reservoir for exemplary purposes) partially or completely circumferentially surrounding the irrigant reservoir 54 or irrigant channel 24. The atomizing reservoir 50 can be embedded in the wall of the irrigation component 120, for example in the wall or case of the irrigant reservoir 54. The irrigation component 120 can be resiliently flexible. The aspirant 58 and irrigant 57 can be delivered by squeezing the irrigation component 120.

The irrigation conduit 90 can be molded into the wall of the irrigation component 120.

The irrigation channel 24 can form a venture 185. The irrigation channel 24 can have an irrigation channel diameter 138. The irrigation channel diameter 138 can be the minimum internal diameter of the irrigation channel 24. The irrigation channel diameter 138 can be less than about 1 cm (0.4 in.), more narrowly less than about 2 mm (0.8 in.), for example about 0.7 mm (0.03 in.).

Figure 21:
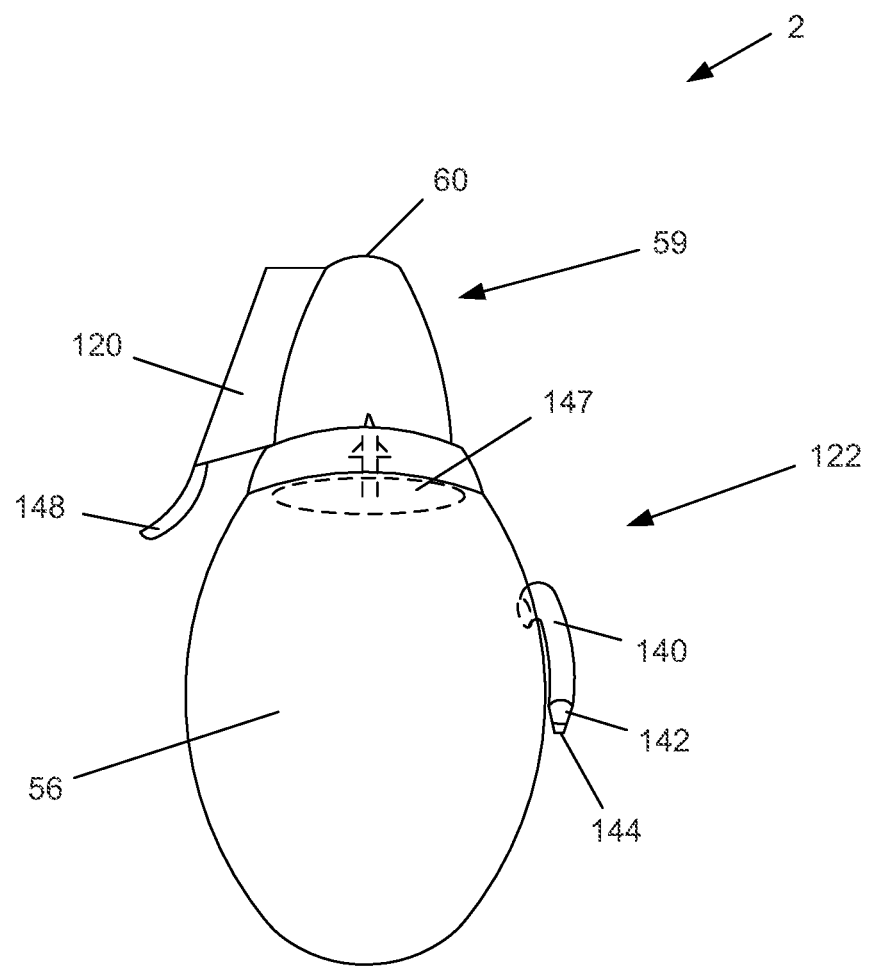
FIG. 21 is a partially see-through view of a variation of the irrigation and aspiration device.

FIG. 21 illustrates that the aspiration reservoir 56 can be a resilient container, such as an elastomeric bulb 114. The aspiration reservoir 56 can have an exhaust conduit 140. The exhaust conduit 140 can be in fluid communication with the aspiration reservoir 56. The exhaust conduit 140 can have an exhaust valve 142 and an exhaust port 144. The exhaust valve 142 can be an check valve 10 configured to flow away from the aspiration reservoir 56.

The nozzle 59 can be integral with or removably attached to the aspiration reservoir 56. The aspiration port 60 nozzle 59 or the aspiration reservoir 56 can have an aspiration valve 146. The aspiration valve 146 can be a check valve 10, for example any check valve 10 stated herein such as an umbrella check valve 147.

The irrigation component 120 can have an irrigation trigger 148. The irrigation trigger 148 can be operated by a single digit 39. When the irrigation trigger 148 is pulled, the irrigation component 120 can dispense irrigant 57.

When the aspiration reservoir 56 is squeezed, the aspiration valve 86 can close and the exhaust valve 142 can open. The aspirant 58 in the aspiration reservoir 56 can be forced out the exhaust conduit 140 and the exhaust port 144. The exhaust valve 142 can be a duckbill valve 70. When the previously-squeezed aspiration reservoir 56 is relaxed, the exhaust valve 142 can close and the aspiration valve 86 can open. Suction can then result at the aspiration port 60 and aspirant 58 can be drawn into the aspiration reservoir 56.

Figure 22:
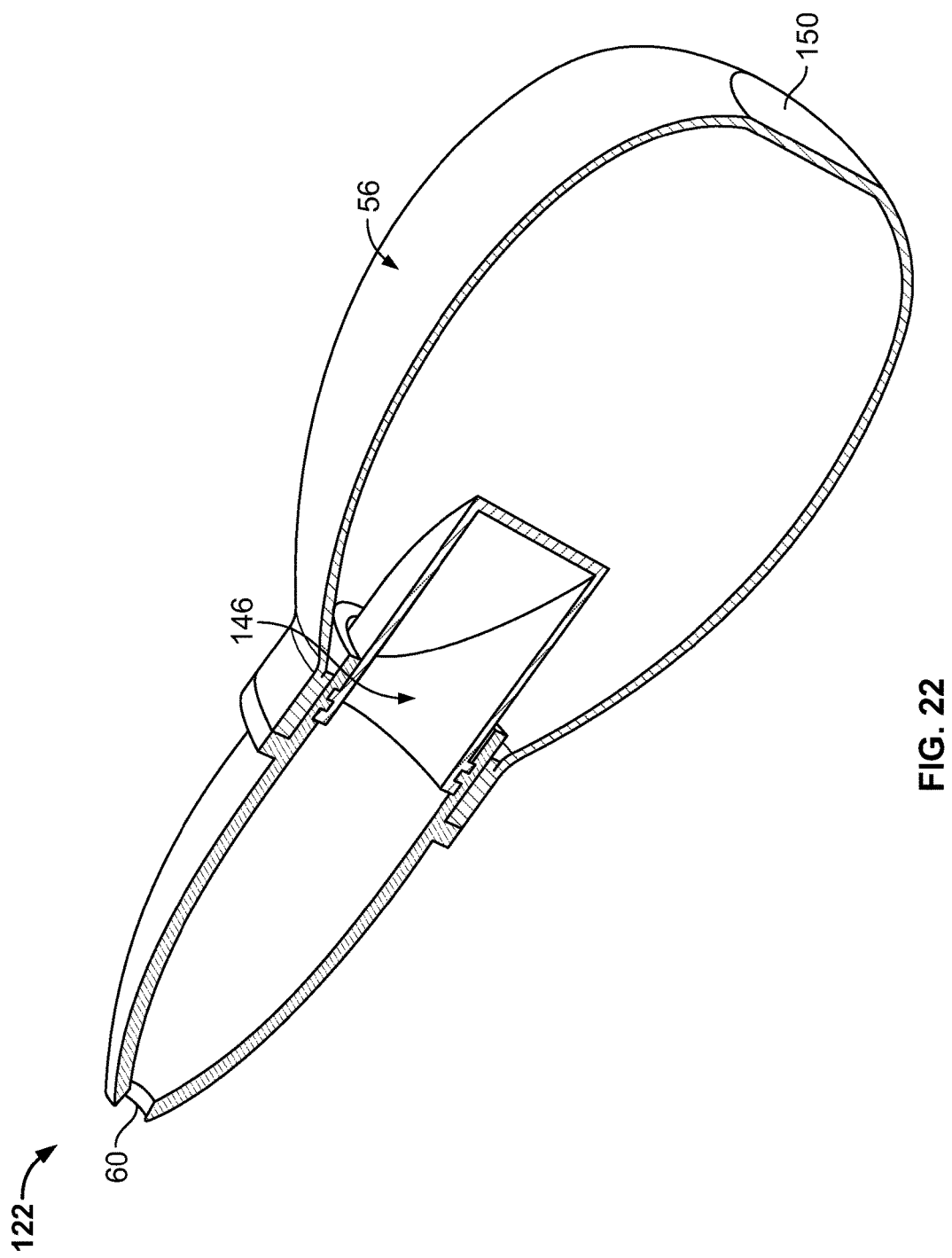
FIG. 22 is a cut-away view of a variation of the aspiration component of the irrigation and aspiration device.

FIG. 22 illustrates that the aspiration valve 86 can be a duckbill valve 70 (the irrigation component 120 is not shown). The aspiration component 122 and/or the device can have a base 150. The base 150 can be configured to enable the device 2 to stand on a flat surface (e.g., a table), for example, keeping the aspiration 60 and atomization 46 and/or irrigation ports 48 off the flat surface.

Figure 23:
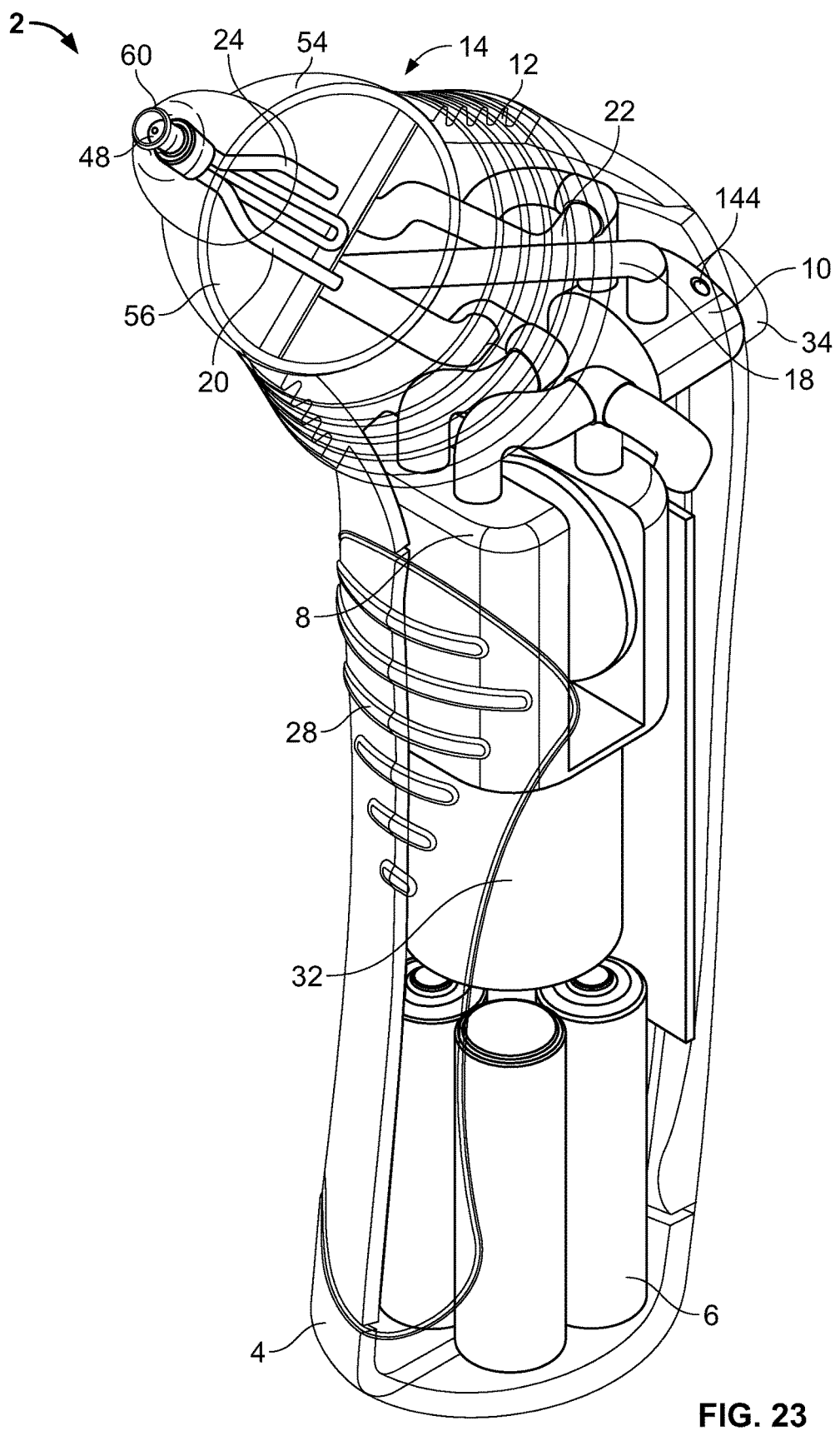
FIGS. 23 and 24 are isometric and side partial cut-away views of a variation of the irrigation and aspiration device.
Figure 24:
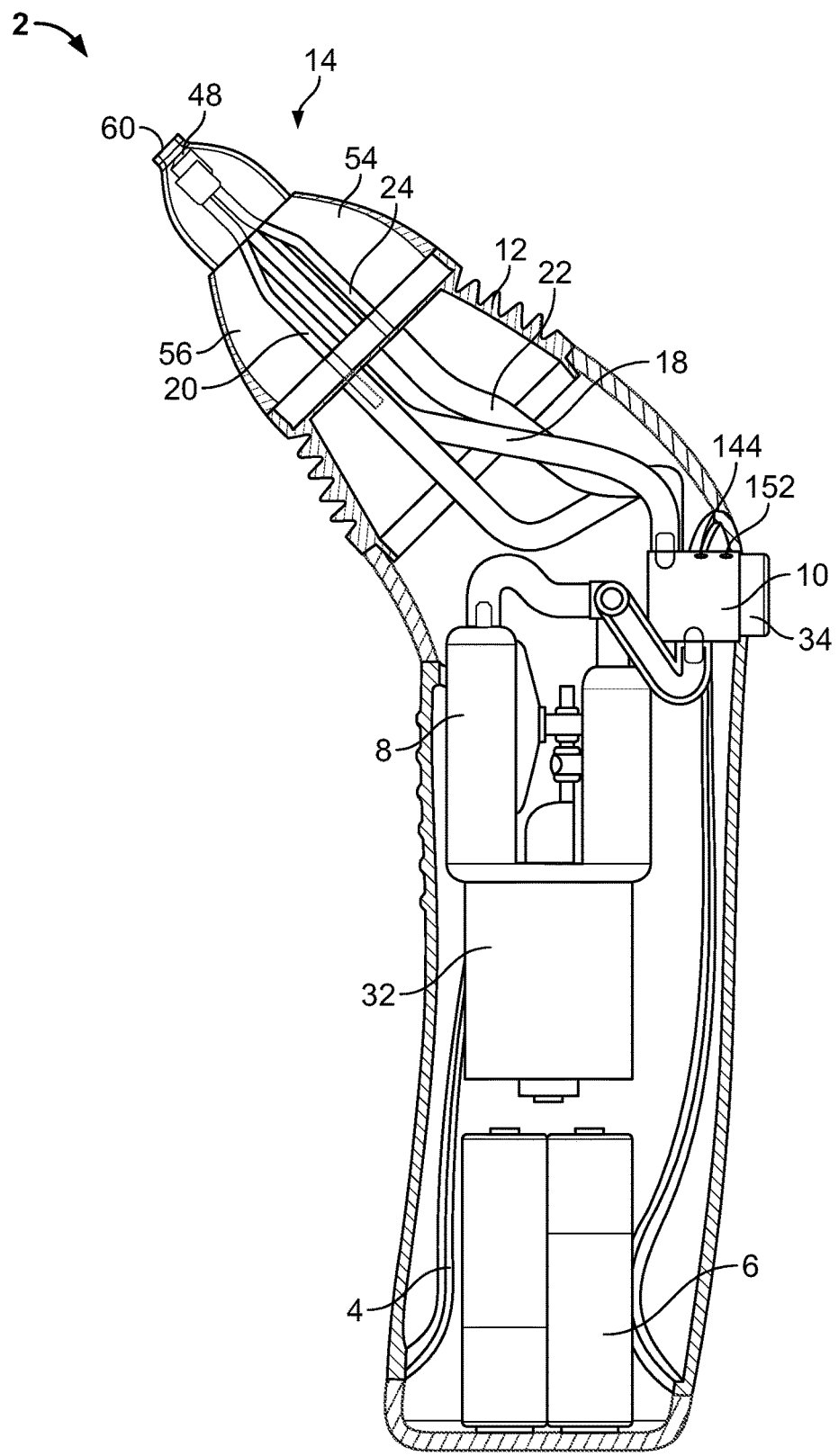

FIGS. 23 and 24 illustrate that the irrigation port 48 can be centrally located within a substantially circular aspiration port 60. The aspiration port 60 and the irrigation port 48 can be at the outer surface of the head 14 and/or the aspiration port 60 and/or the irrigation port 48 can be recessed within the head 14.

The head 14 can have the aspiration reservoir 56 and the irrigation reservoir 54. The aspiration reservoir 56 can be in direct fluid communication with the aspiration port 60.

The device 2 can have one or more valves 10 configured to control the irrigation delivery pressure and/or the aspiration suction pressure. The valves 10 can be actuated by one or more buttons 34, such as a press-button 34, as shown. The valves 10 can be in fluid communication with the pump 8 and the irrigant pressure line 22, aspirant pressure line 18 and atomizing channel 20, and an exhaust port 144 and intake port 152. In closed positions, the valves 10 can bleed or release pressure to the exhaust port 144 and/or suction through the intake port 152. In opened positions, the valves 10 can delivery positive pressure from the pump 8 to the irrigant pressure line 22 and the atomizing channel 20, and negative pressure from the pump 8 to the aspirant pressure line 18.

The pump can be a piston 124 and/or diaphragm pump 8, such as the dual diaphragm pump 8, as shown in FIGS. 23 and 24.

The aspirant reservoir 56 and/or irrigant reservoir 54 can be in the head 14. The aspirant reservoir 56 and/or irrigant reservoir 54 can be in direct fluid communication (e.g., not via a separate channel) with the aspiration port 60 and/or irrigation port 48, respectively. The lack of a separate channel connecting the aspirant 56 and/or irrigation reservoir 54 and the aspiration port 60 and/or irrigation port 48, respectively, can obviate the need to clean the separate channel.

The device 2 can have a portable power source 6, such as batteries as shown in FIGS. 23 and 24. For example, the device 2 can have 1, 2, 3 or 4 AA-sized cells. The cells can be inserted through a battery door 30 in the bottom of the device.

The pump 8 can be connected to a control 32 or controller, such as a motor. The control 32 can have a microprocessor configured to regulate the motor speed to control irrigant delivery pressure and/or aspirant suction pressure. The aspirant suction pressure can be, for example, from about 80 mm Hg (1.5 psi) to about 120 mm Hg (2.32 psi). The control 32 can receive an input from the button 34. The microprocessor can analyze the button position to control the motor speed and/or valve 10 position.

Figure 25:
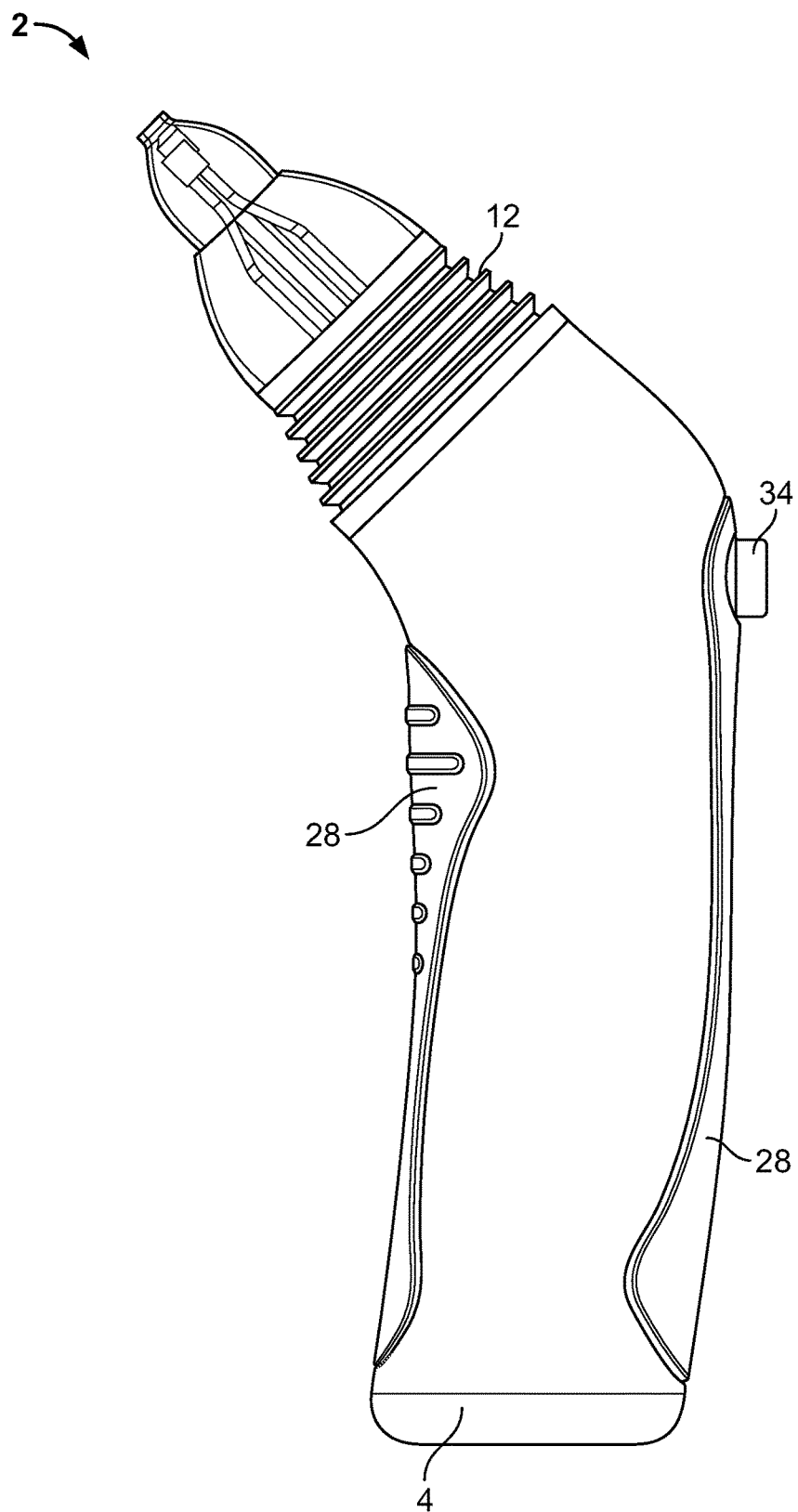
FIGS. 25 and 26 are side and front views of the irrigation and aspiration device of FIGS. 23 and 24.
Figure 26:
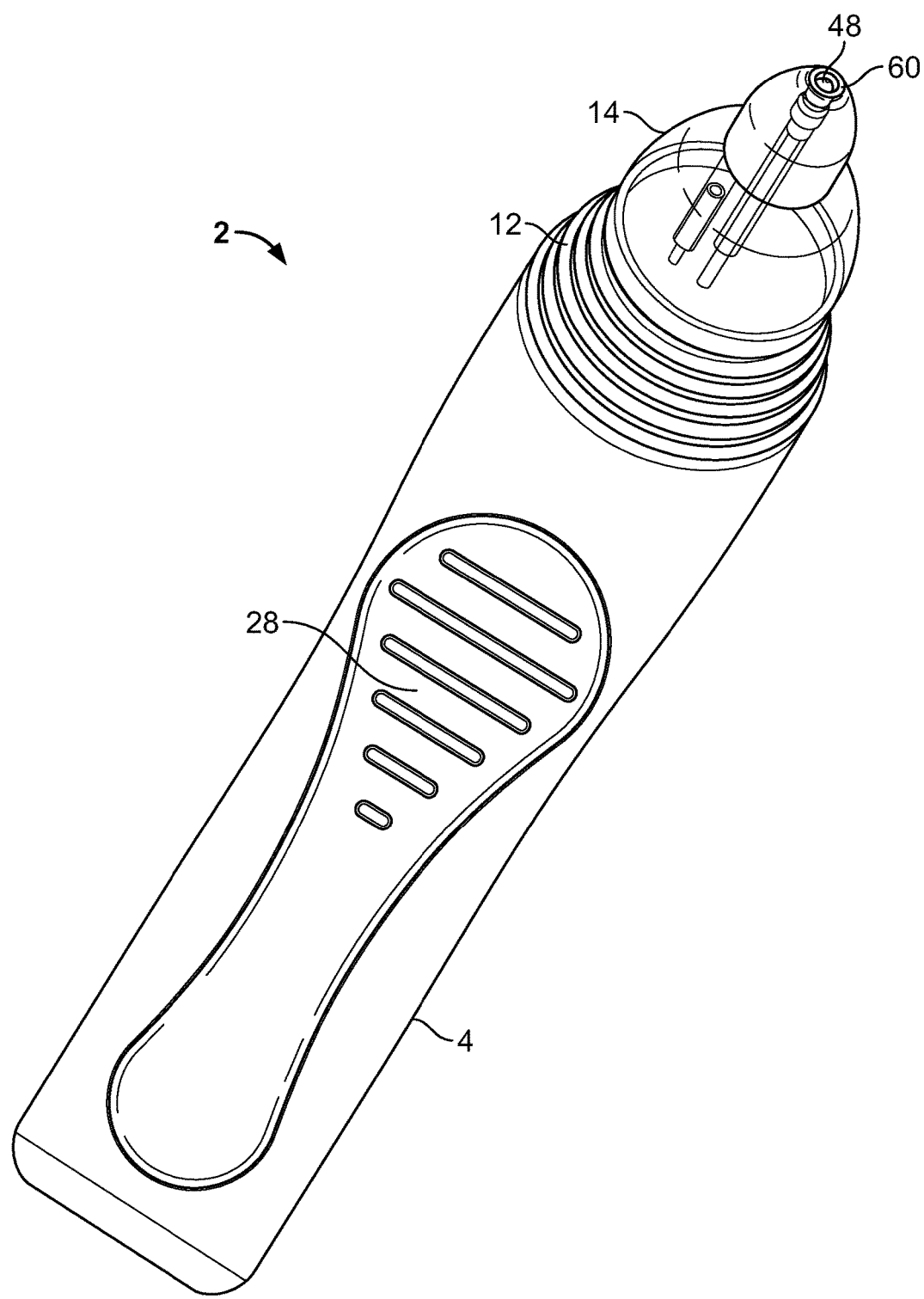

FIGS. 25 and 26 illustrate that the grip pads 28 can be ergonomically placed on the front and back of the body 4. The grip pads 28 can have ridges or texturing. The grip pads 28 can be made from metal, soft plastic or rubber. The head 14 can be opaque, transparent and/or translucent. The head 14 can be removably attached to the neck 12 and/or the neck 12 can be removably attached to the remainder of the body 4.

Figure 27:
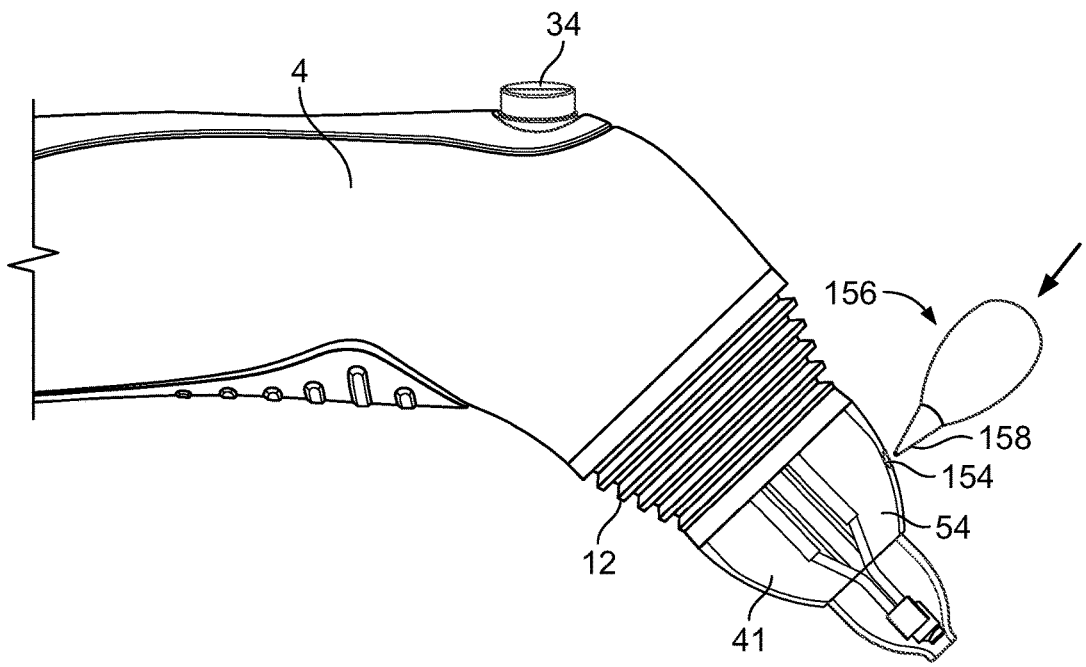
FIGS. 27 and 28 illustrate various methods for filling the irrigation and aspiration device with irrigant.

FIG. 27 illustrates that the irrigant 57 can be refilled. The irrigant reservoir 54 can have an irrigant reservoir seal 154 against the outer wall of the irrigant reservoir 54. For example, the irrigant reservoir seal 154 can be plastic. The irrigant reservoir seal 154 can be self sealing and/or manually controlled to open and close.

An external irrigant container 156 can have fresh irrigant 57. The external irrigant container 156 can have a container spout 158 configured to insert into the irrigant reservoir 54 through the irrigant reservoir seal 154. The external irrigant container 156 can be advanced into the irrigant reservoir seal 154, as shown by arrow. The contents of the external irrigant container 156 can then be deposited into the irrigant reservoir 54, for example by squeezing the external irrigant container 156 and/or by opening a pressure release port (not shown) on the external irrigant container 156. The irrigant 57 in the external irrigant container 156 can then be transferred into the irrigant reservoir 54. The external irrigant container 156 can then be removed from the irrigant reservoir seal 154 and the irrigant reservoir seal 154 can close.

Figure 28:
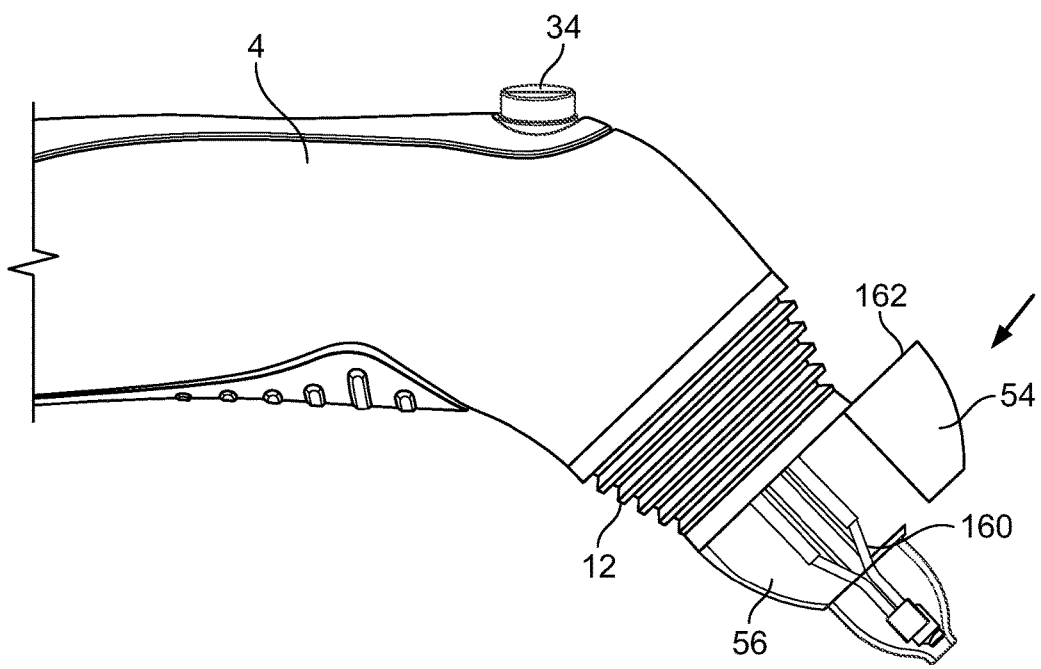

FIG. 28 illustrates that the head can have a cartridge receptacle 160 configured to removably attach to an irrigant cartridge 162. The cartridge receptacle 160 can have ports, hooks, latches, pegs, or combinations thereof that can removably attach to the same on the irrigant cartridge 162. When the irrigant cartridge 162 is not attached, the cartridge receptacle 160 can define a void substantially equivalent to the configuration of the irrigant cartridge 162.

The irrigant cartridge 162 can have the irrigant reservoir 54 that can contain irrigant 57. The irrigant cartridge 162 can be inserted into the irrigant receptacle 160, as shown by arrow. The irrigant cartridge 162 can have one or more ports (not shown) that can engage the irrigant pressure line 22 and/or irrigant channel 24 when the irrigant cartridge 162 is attached to the cartridge receptacle 160. The ports 118 on the irrigant cartridge 162 can be closed or covered, for example by adhered aluminum foil when the irrigant cartridge 162 is not in the cartridge receptacle 160. For example, the cartridge receptacle 160 can have one or more fangs or tubes configured to pierce the irrigant cartridge 162 (e.g., through a foil or seal) and be in fluid communication with the interior of the irrigant cartridge 162 and pressurize or depressurize the irrigant cartridge 162 and/or withdraw irrigant from the irrigant cartridge 162.

A first irrigant cartridge 162 can be removed from the irrigant receptacle 160 and replaced with a second irrigant cartridge 162, for example when the first irrigant cartridge 162 is empty.

In another variation, when the irrigant reservoir 54 is empty and/or the aspirant reservoir 56 is full or otherwise in need of emptying or cleaning, the entire head 14 can be removed from the neck 12 and replaced with a second head 14 containing more irrigant 57 in the irrigant reservoir 54. Likewise, the aspirant reservoir 56 can be removed (similar to the sole removal of the irrigant cartridge 162). The head 14 and/or irrigant reservoir 54 and/or aspirant reservoir 56 and/or the device 2 can be washed, for example, by hand and/or in a dishwasher. The body 4 and/or the device 2 can be waterproof.

Figure 29:
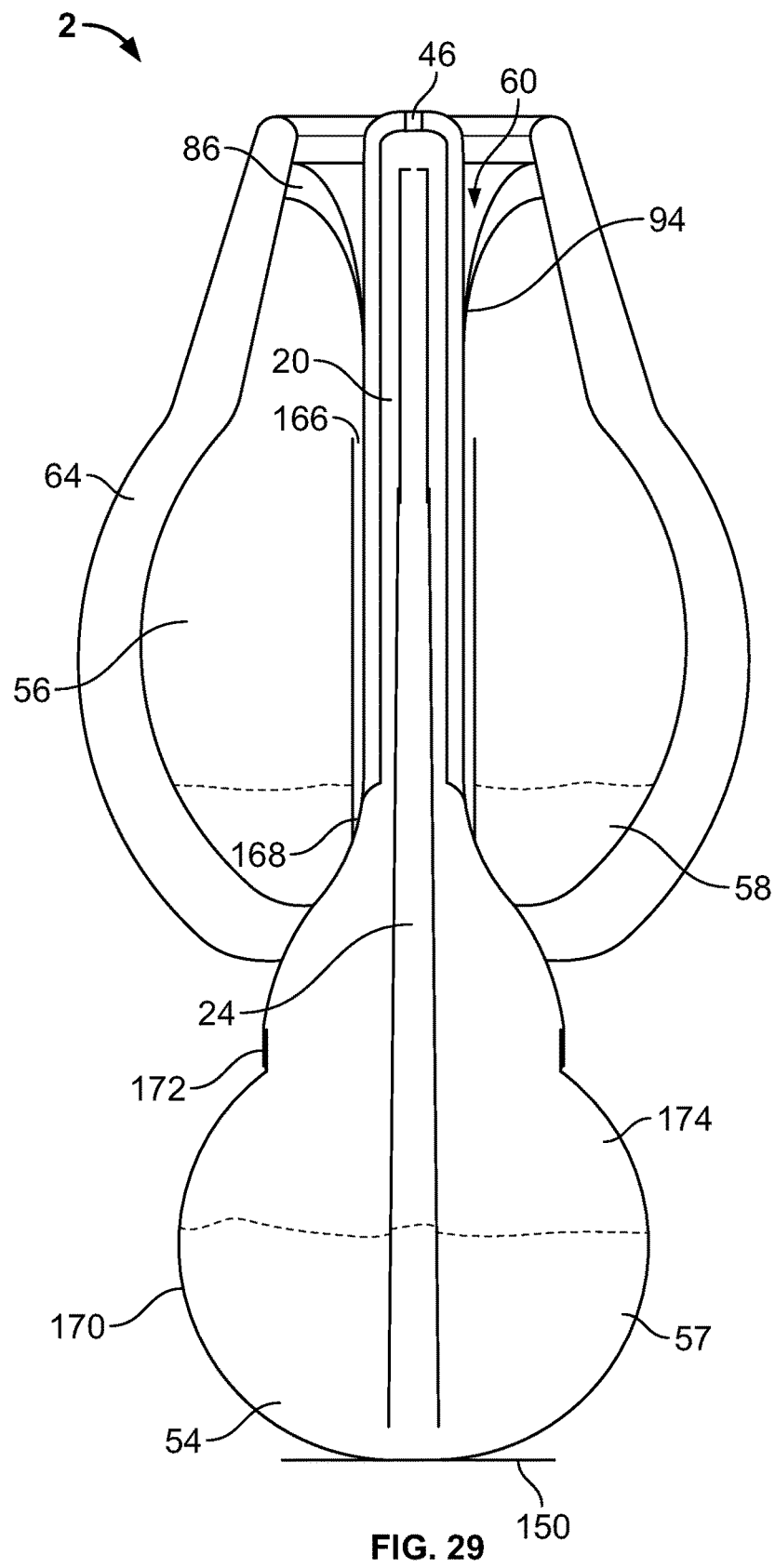
FIG. 29 is a cut-away view of a variation of the irrigation and aspiration device.

FIG. 29 illustrates that the aspiration reservoir 56 can be in a resilient vacuum bulb 164. The vacuum bulb 164 can be elastomeric. The aspiration reservoir 56 can be in fluid communication with the irrigation reservoir 54, for example, via an irrigation-aspiration port 166. The irrigation-aspiration port 166 is configured to be away from the aspirant fluid level in the aspirant reservoir 56.

An irrigation-aspiration valve 168 can be in fluid communication with the aspiration reservoir 56 and the irrigation reservoir 54. The irrigation-aspiration valve 168 can be a check valve 10. The irrigation-aspiration valve 168 can be a valve 10 permitting flow only from the aspiration reservoir 56 to the irrigation reservoir 54 and preventing flow from the irrigation reservoir 54 to the aspiration reservoir 56.

The aspiration valve 146 can be a one-way check valve 10 permitting flow into the aspiration reservoir 56.

The irrigation reservoir 54 can be in an irrigation container 170. The irrigation container 170 can be rigid, for example a plastic bottle. The irrigation container 170 can be integral with or removably attachable to the remainder of the device at an attachable reservoir joint 172. The atomization fluid reservoir 174 can be the top of the irrigation reservoir 54, above the level of the irrigant 57.

The base 150 can extend from the reservoir container. The base 150 can be wider than the widest portion of the remainder of the device 2.

Squeezing the vacuum bulb 164 can atomize and eject irrigant 57 from the atomization port 46. For example, when the vacuum bulb 164 is squeezed, the irrigation-aspiration valve 163 can open and the irrigation reservoir 54 can be pressurized via the irrigation-aspiration port 166. The increased pressure in the irrigation reservoir 54 can cause the irrigant 57 to flow through the irrigation channel 24. The increased pressure in the irrigation reservoir 54 can also force gas in the irrigation reservoir 54 (e.g., above the irrigant 57) through the atomization channel 20.

Relaxing the previously squeezed irrigation-aspiration valve 168 can suction aspirant 58 into the aspiration reservoir 56. For example, the irrigation-aspiration valve 168 can close. The negative pressure in the aspiration reservoir 56 can draw in aspirant 58 by opening the aspiration seal 94 in the aspiration port 60.

Figure 30:
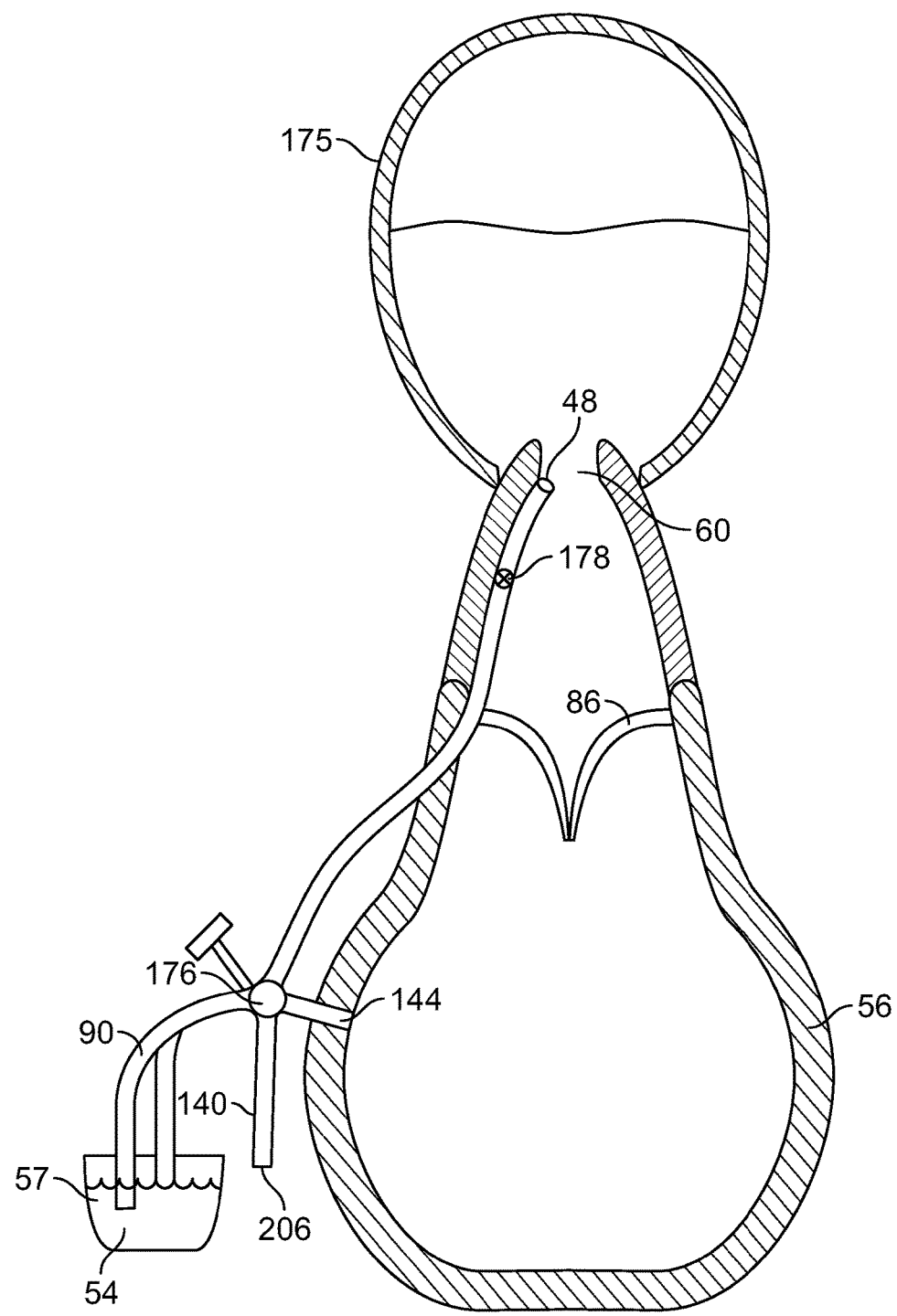
FIG. 30 is a partial cut-away view and partial schematic diagrams of a variation of the irrigation and aspiration device.

FIG. 30 illustrates that one or more covers 175 can be configured to fit over the aspiration 60 and/or irrigation 48 and/or atomization ports 46.

The device 2 can have a manually or automatically controllable dual exhaust valve 176. The dual exhaust valve 176 can be passive or active. The dual exhaust valve 176 can regulate excessive fluid pressure from the aspiration reservoir 56 and/or the irrigant reservoir 54 to an exhaust conduit 140. The excessive fluid pressure can exit the exhaust conduit 140 as an exhaust flow, shown by arrow.

An irrigation valve 178 can regulate flow from the irrigant reservoir 54 to the irrigation port 48. The irrigation valve 178 can be configured to prevent the irrigant 57 from exiting the irrigation port 48 at an excessive pressure. The velocity of the irrigant 57 flow stream can be prevented from exiting the device 2 at an excessive velocity.

Figure 31:
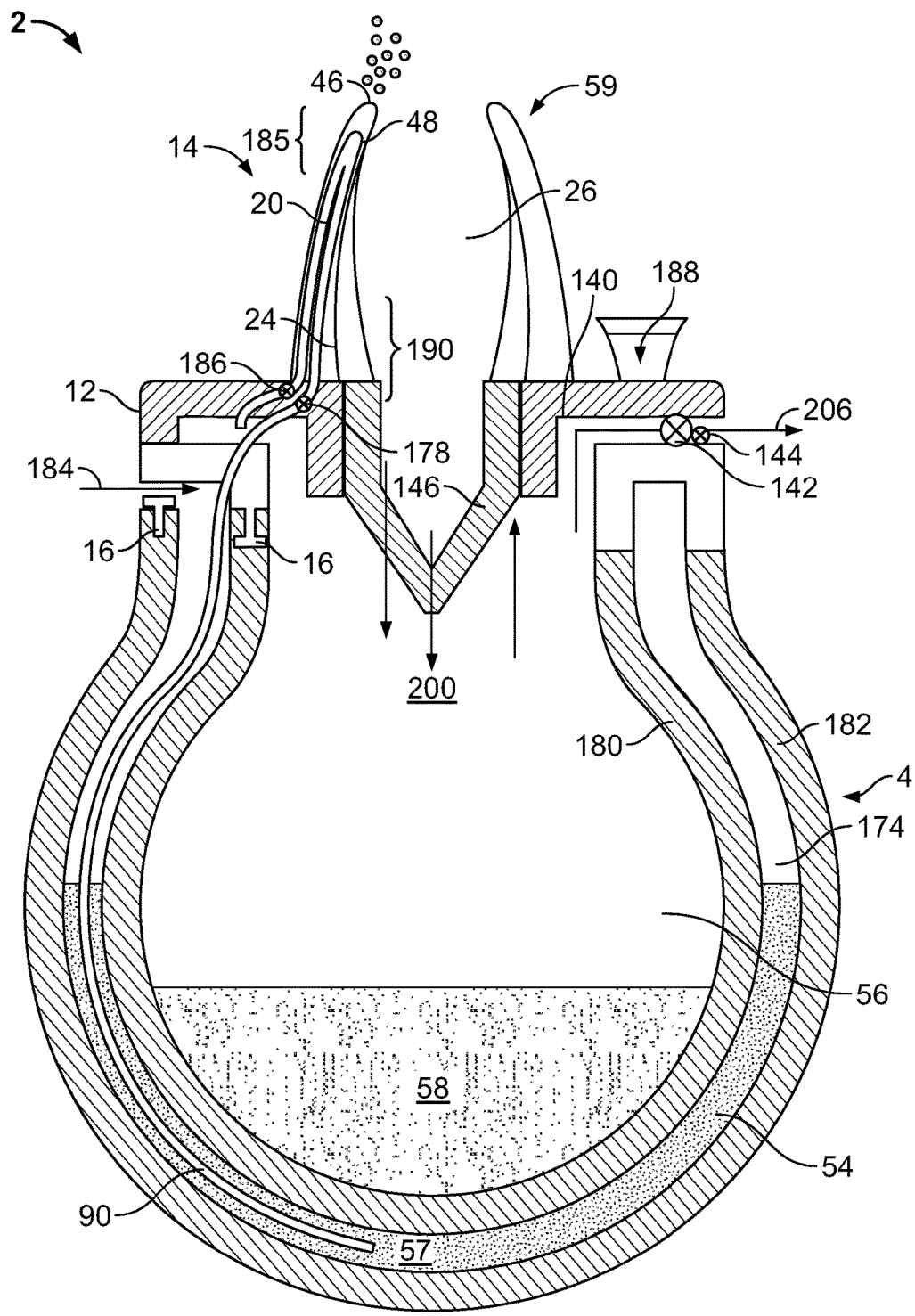
FIG. 31 is partial cut-away view and partial schematic diagrams of a variation of the irrigation and aspiration device.
Figure 32:
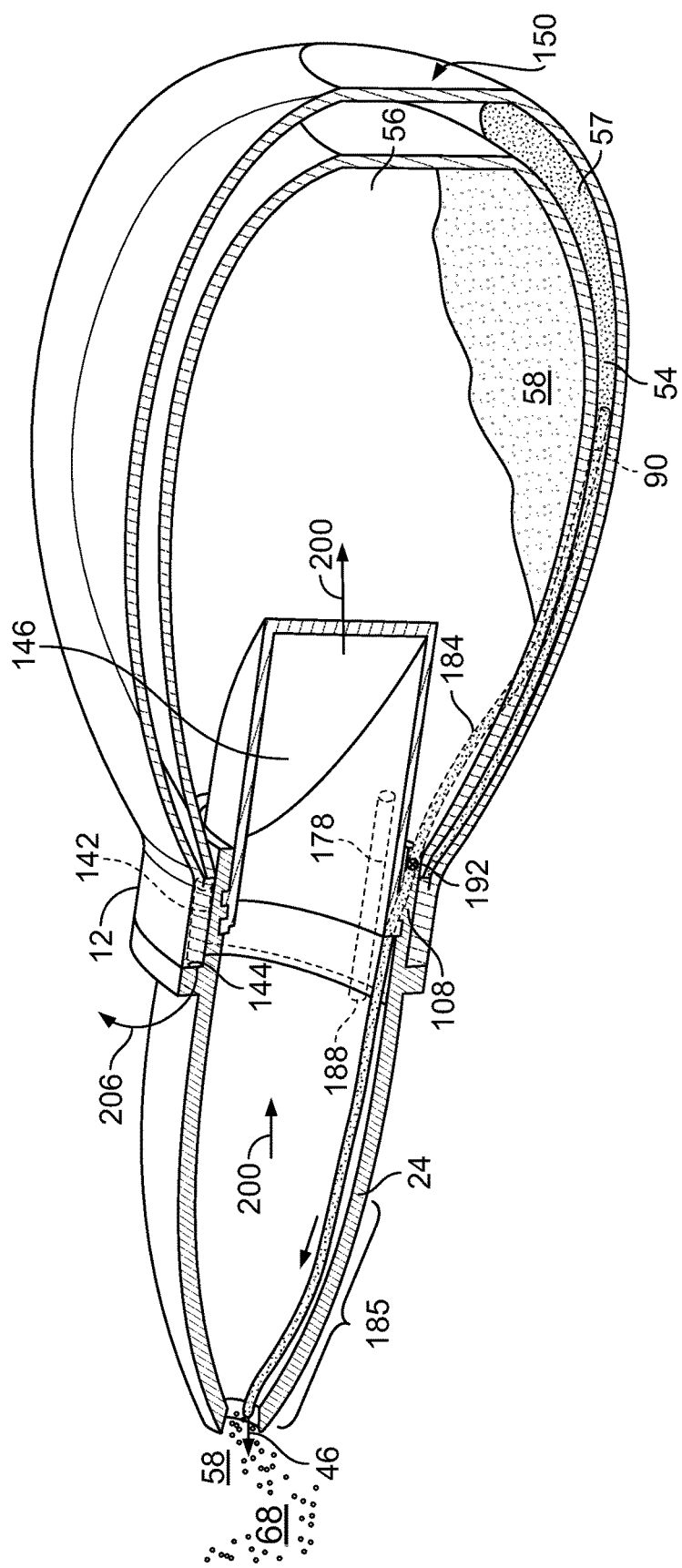
FIG. 32 is partial cut-away view, partial see-through view and partial schematic diagrams of a variation of the irrigation and aspiration device.

FIGS. 31 and 32 illustrate that the aspirant reservoir 56 can be in an inner irrigant reservoir wall 180. The irrigant reservoir 54 can be between an inner irrigant reservoir wall 180 and an outer irrigant reservoir wall 182. The inner irrigant reservoir wall 180 and the outer irrigant reservoir wall 182 can be rigid, resilient or deformable.

The device 2 can have an atomization intake port 184 on the outside surface of the device 2. The atomization intake port 184 can be in fluid communication with the atomization fluid reservoir 174. The atomization intake port 184 can have a check valve 10 configured to allow one-way flow from the atomization intake port 184 to the atomization fluid reservoir 174.

The atomization valve 186 can regulate flow between the irrigant reservoir 54 to the atomization channel 20. The atomization channel 20 can have a venturi 185 configuration adjacent to the irrigation port 48. The venturi 185 can atomize the irrigant 57 and/or increase the speed of the atomization gas.

The irrigant valve 178 can regulate flow between the irrigant reservoir 54 and the litigant channel 24. The irrigant valve 178 can be a check valve 10. The irrigant valve 178 can prevent flow from the irrigant channel 24 to the irrigant reservoir 54. The irrigant valve 178 can permit substantially free flow from the irrigant reservoir 54 to the irrigant channel 24. The irrigant valve 178 can restrict the flow from the irrigant reservoir 54 to the irrigant channel 24 except under high pressure differentials, for example a pressure differential greater than about 25 mmHg (0.5 psi), more narrowly a pressure differential greater than about 100 mmHg (2 psi), more narrowly a pressure differential greater than about 260 mmHg (5 psi), more narrowly a pressure differential greater than about a pressure differential greater than about 760 mmHg (14.7 psi), for example for a pressure differential greater than about 1600 mmHg (30 psi).

An litigant intake port 188 can be in fluid communication with the irrigant reservoir 54. The irrigant intake port 188 can have a check valve 10 configured to allow one-way flow from the irrigant intake port 188 to the irrigant reservoir 54. The irrigant reservoir 54 can be filled by introducing irrigant 57 through the irrigant intake port 188.

The aspiration channel 26 can have a valve transition zone 190. The valve transition zone 190 can be configured as a smooth transition from the inner wall of the aspiration channel 26 to the inner wall of the aspirant valve 146.

An exhaust valve 142 can regulate flow between the aspirant reservoir 56 and the exhaust port 144. The exhaust port 144 can be covered and uncovered by the user (e.g., by a digit 39, such as the thumb 42) during use. The exhaust can flow from the aspirant reservoir 56 and out the exhaust port 144, as shown by arrow.

The device 2 shown in FIGS. 31 and 32 can be squeezed to deliver the irrigant 57. Releasing the device 2 from a squeezed configuration can aspirate.

FIG. 32 shows that the irrigant 57 and atomization fluid can be mixed a mixing valve 192. The mixing valve 192 can be upstream from the atomization port 46.

FIG. 33 illustrates that the device 2 can have a body 4 that can be attached to the head 14 with a lead 194. The lead 194 can carry the irrigant pressure line 22 and/or irrigant channel 24, aspirant pressure line 18 and/or aspirant channel 26, atomization channel 20 or combinations thereof. The lead 194 can be flexible. The lead 194 can be retractable into the body 4, for example with a spring-loaded retraction mechanism. The lead 194 can be coiled. The head 14 can have a removably attached aspirant reservoir 56 and/or irrigant reservoir 54 (not shown separately).

The body 4 can have a flat base 150. The body 4 can be attached to a surface such as a flat surface (e.g., floor, table, crib), for example with screws, nails, brads, bolts or combinations thereof. The body 4 can be weighted with ballast and/or have a clamp (e.g., to stabilize).

Figure 34A:
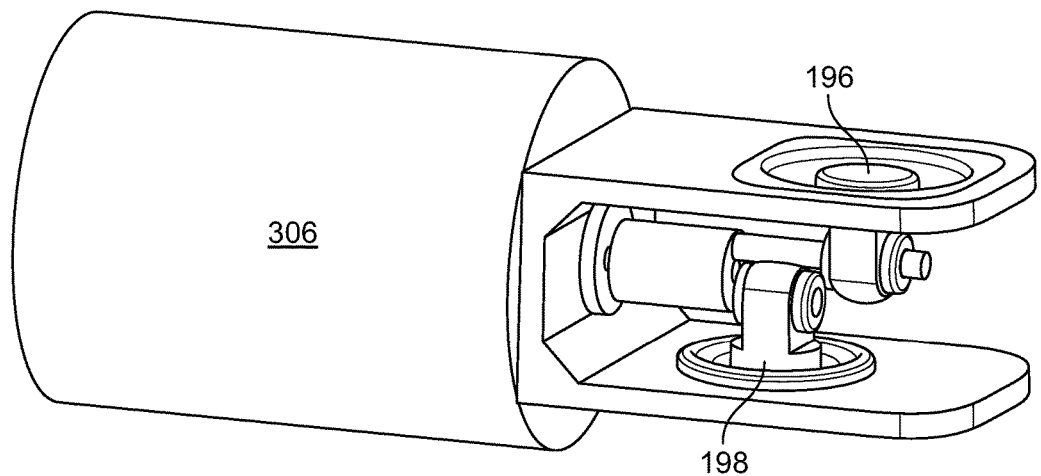
FIGS. 34a-c are isometric, top and side views, respectively, of a variation of a dual diaphragm pump.
Figure 34B:
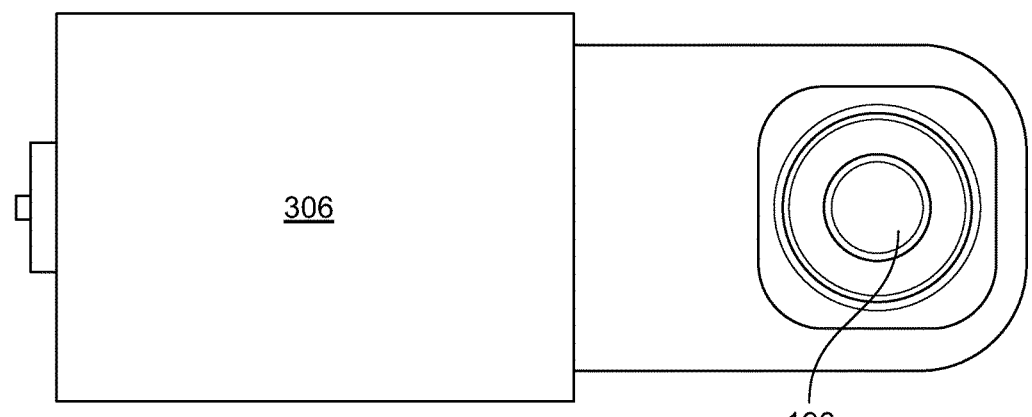
Figure 34C:
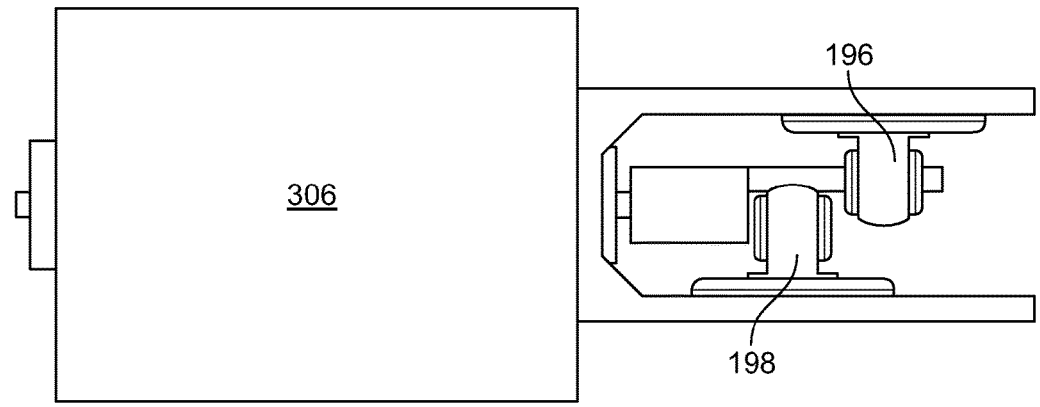

FIGS. 34a through 34c illustrate that the fluid control 32 and pump 8 can have a motor 306 attached to a first 196 (and/or second diaphragm 198). The pump 8 can be a piston 124 or diaphragm pump 8 (i.e., a membrane pump, positive displacement pump). The pump 8 can be a boxer pump 8, having at least two oppositely-oriented oscillating shafts, rods, or membranes. The pump 8 can be or have a compressed gas (e.g., air, carbon dioxide, nitrogen) canister that can be configured to controllably release the compressed gas.

The pump 8 can be similar in geometry to a Daco pump 8. The pump 8 can have doubled-up diaphragms. The pump 8 can be driven by a motor 306 that can be driven by the power source 6. The device 2 can produce a maximum irrigant volumetric flow rate of at least about 9,000 cc/m, more narrowly at least about 12,000 cc/m, yet more narrowly at least about 15,000 cc/m.

The pump 8 can have one or more blowers, turbines, fans, diaphragms, bellows, or combinations thereof. The pump 8 can be manually and/or electrically powered. The pump 8 can be attached to an AC or DC-driven motor.

Figure 35:
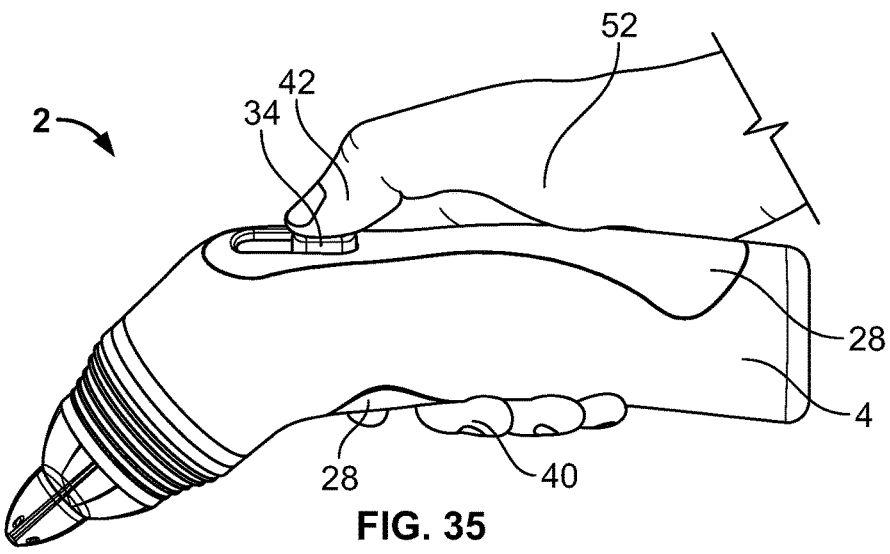
FIGS. 35 through 37 illustrate a variation of a method of using a variation of the irrigation and aspiration device.

FIG. 35 illustrates that a user can ergonomically hold the body 4 in a single hand. The user can rest a digit 39, such as the thumb 42, on the button 34. The pain 52 and/or other fingers 40 can substantially or completely rest on the grip pads 28.

Figure 36:
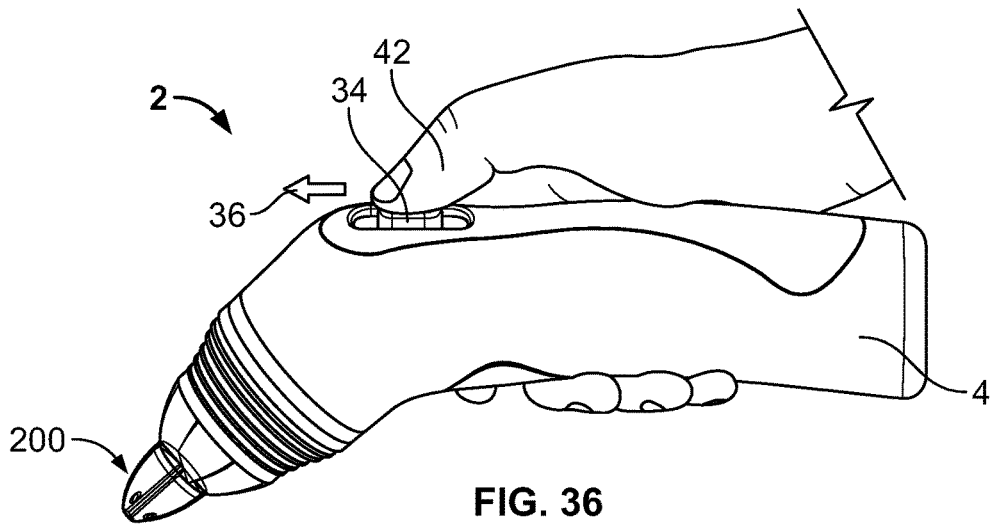

FIG. 36 illustrates that the thumb 42 can slidably translate the button 34, as shown h arrow. The slidable translation 36 of the button 34 can control irrigation or aspiration. As shown for example, sliding the button 34 can actuate the device 2 to create a suction resulting in aspirant flow 200, as shown by arrow. The distance the button 34 is slidably translated 36 can directly correlate to the pressure of the aspiration or irrigation.

Figure 37:
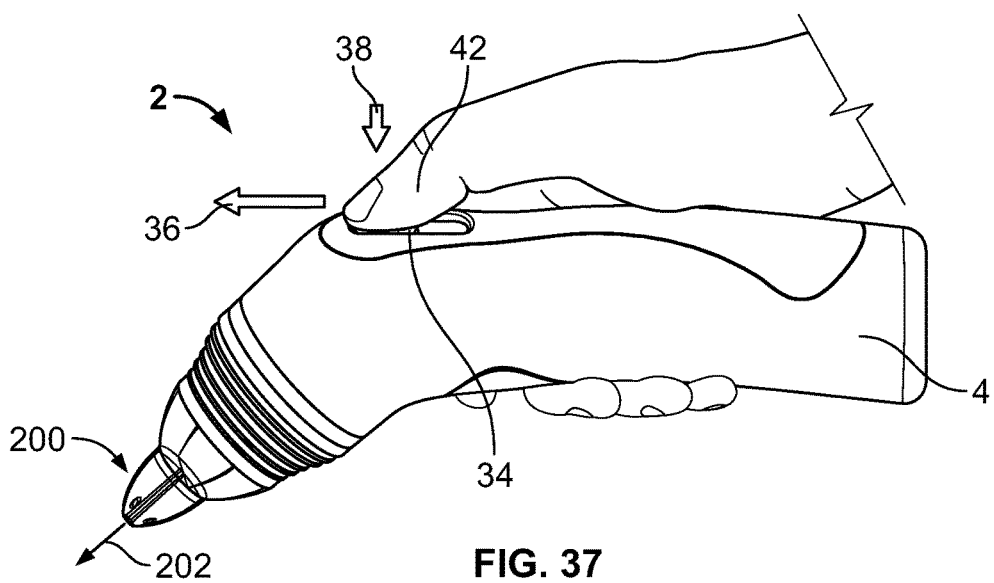

FIG. 37 illustrates that the thumb 42 can slidably translate 36, as shown by arrow, and concurrently depressingly translate 38, as shown by arrow, the button 34. The depressing translation 38 can control the other of the irrigation or aspiration not controlled by the sliding translation 36. Sliding and depressing the button 34 can actuate the device 2 to create a suction resulting in aspirant flow 200, as shown by arrow, and resulting in a pressured fluid delivery resulting in the irrigant flow 202, as shown by arrow.

Figure 38:
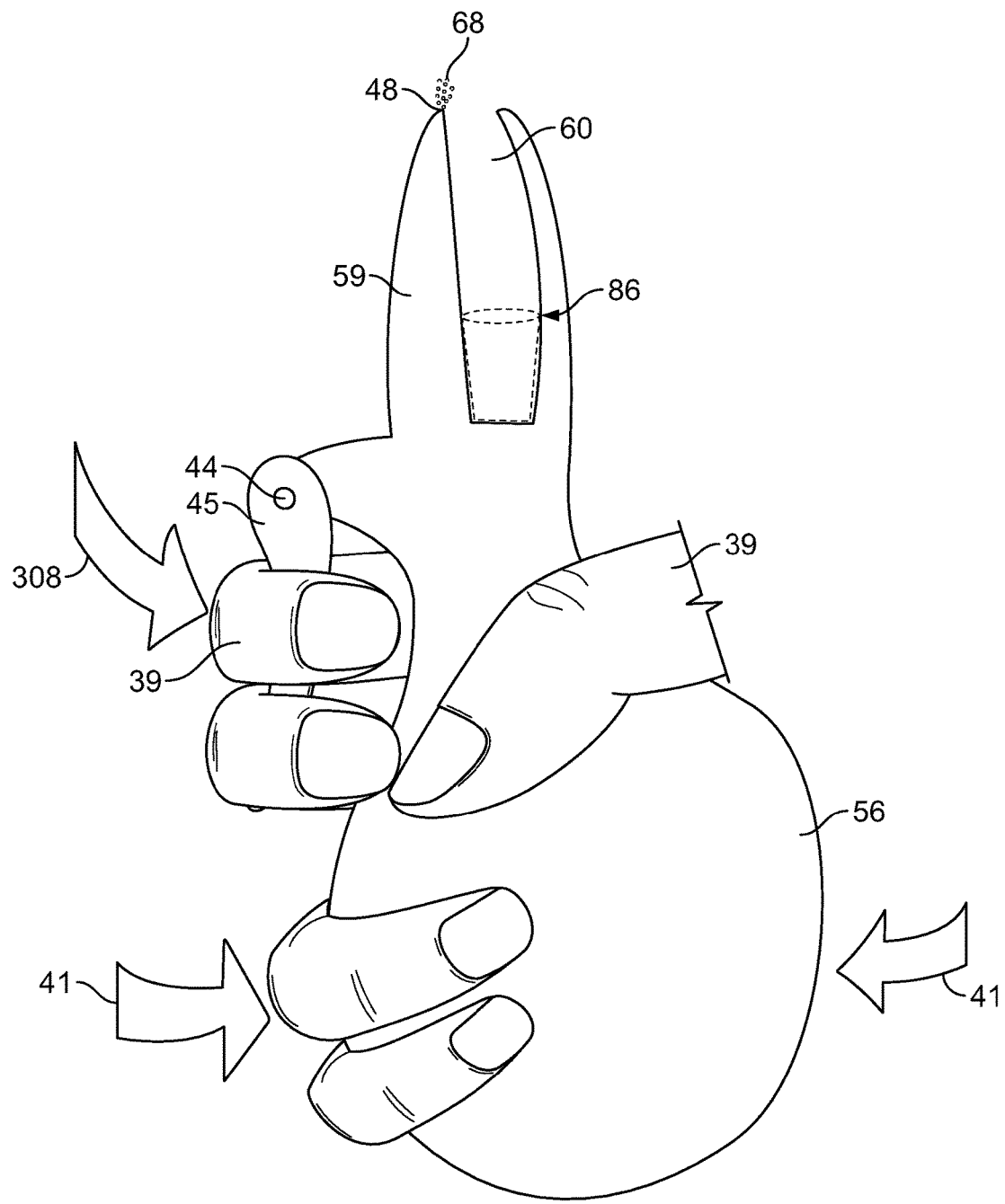
FIG. 38 illustrates a variation of a method of using a variation of the irrigation and aspiration device.

FIG. 38 illustrates that the device 2, such as the variation shown in FIG. 21, can be actuated to irrigate by rotating 308 a trigger 45 on a hinge, for example with one or more digits 39 (e.g., the forefinger and/or middle finger). The aspirant reservoir 56 can be completely or partially emptied by compressing 41, as shown by arrows, the aspirant reservoir 56, for example with the thumb 42, ring finger, pinky and palm 52. The aspirant 58 can be drawn into the aspiration port 60 by releasing the compressed aspirant reservoir 56.

Variations of the device 2, such as those shown in FIGS. 29 through 32, can be actuated by squeezing (e.g., for irrigation) and releasing (e.g., for aspiration) all or part of a resilient portion of the device 2, such as a bulb 114.

Figure 39:
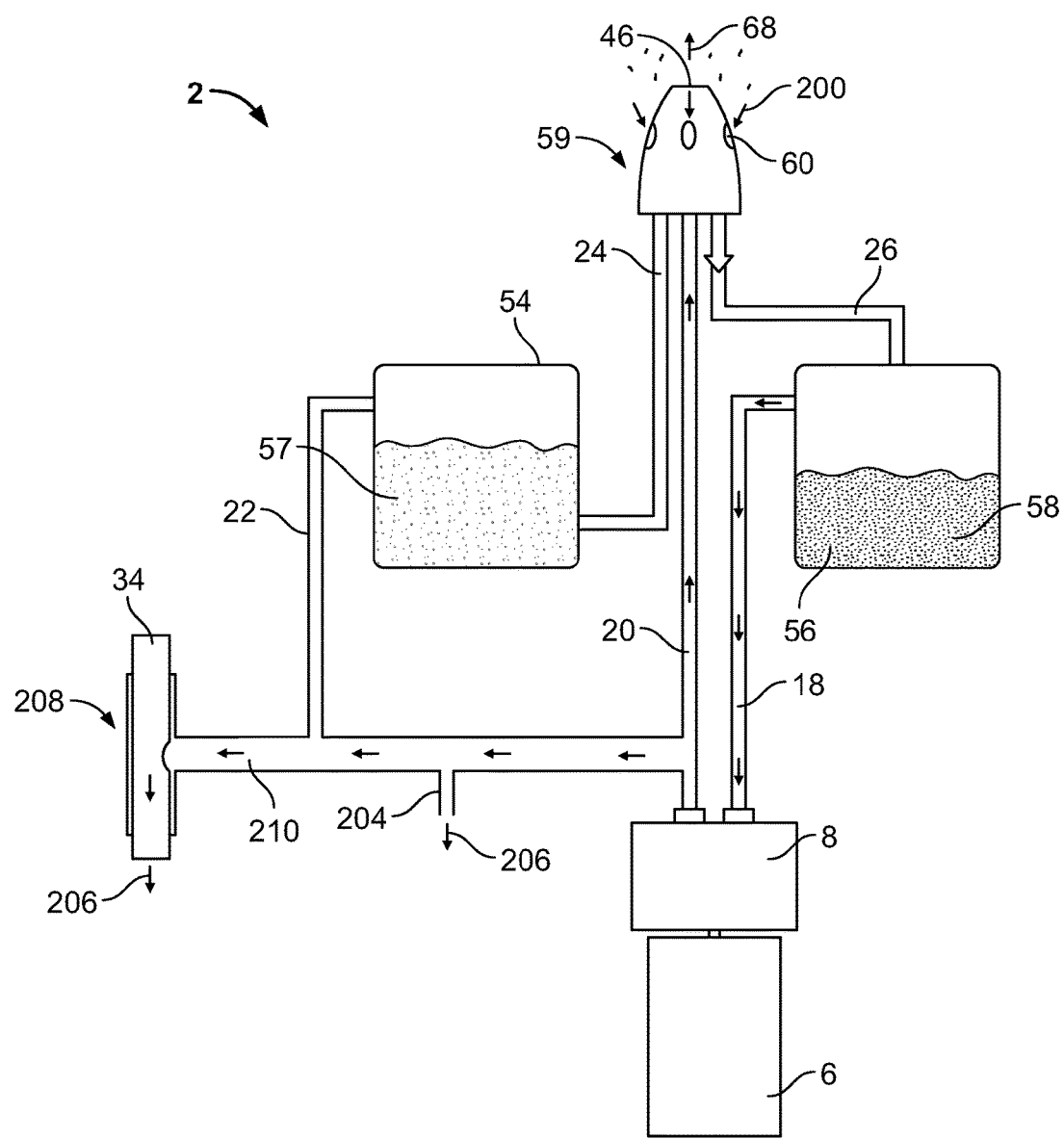
FIGS. 39, 40, 41 and 44 are schematic diagrams of a variation of the irrigation and aspiration device in various configurations.

FIG. 39 illustrates that the pump 8 can draw air from the aspirant reservoir 56. The resulting vacuum can draw aspirant flow 200, as shown by arrows, through the aspiration ports 60. The irrigant pressure line 22 can have an excess flow port 204. The excess flow port 204 can bleed excess pressure out of the irrigant pressure line 22 as exhaust flow 206.

The device 2 can have a first valve 208 in a controlled exhaust line 210 in fluid communication with the irrigant pressure line 22. The first valve 208 can be actuated by a button 34. The button 34 can be in a position configured to produce aspiration and no irrigation. All or part of the exhaust pressure from the pump 8 can flow out of the device 2 as exhaust flow 206, as shown by arrows. All or part of the exhaust pressure from the pump 8 can flow throw the atomization channel 20 and out the atomization port 46. The flow through the atomization port 46, as shown by arrows, can, for example, prevent aspirant from passively flowing into the atomization port 46. The irrigation pressure line 22 can be significantly smaller than the controlled exhaust line 210. For example, no or unsubstantial flow can be generated in the irrigant pressure line 22 while the controlled exhaust line 210 is open.

Figure 40:
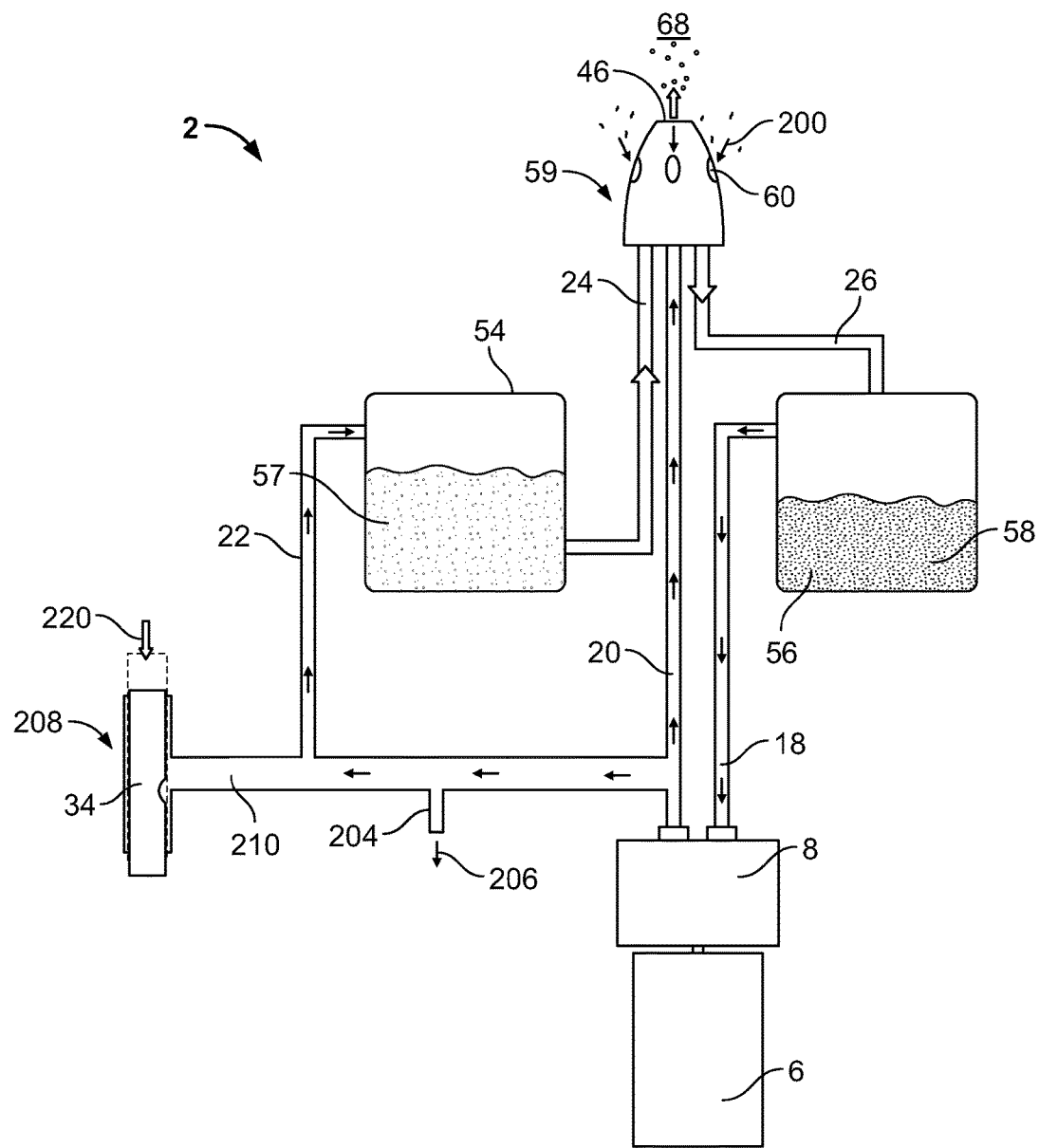
Figure 41:
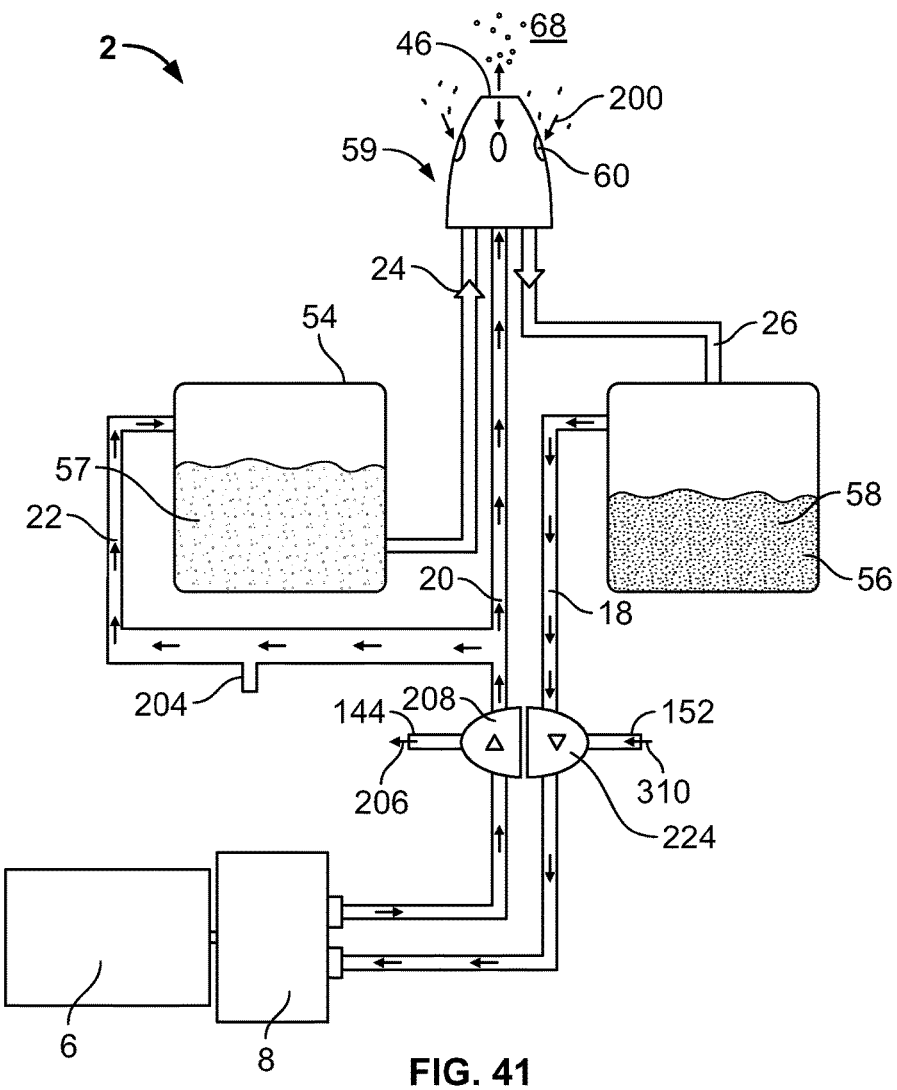
Figure 42:
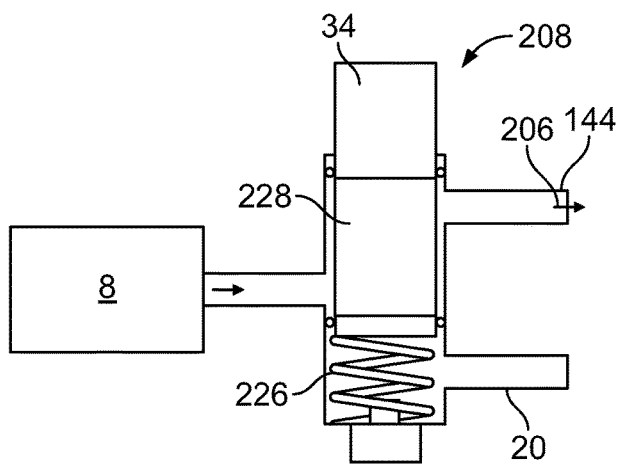
FIGS. 42 and 43 are schematic drawings of a variation of the first valve and the surrounding channels of FIG. 41 in first and second configurations, respectively.
Figure 43:
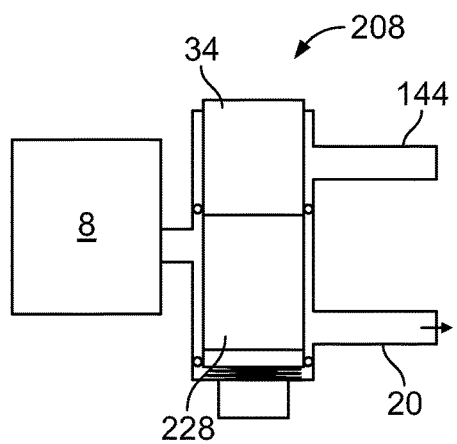

FIG. 40 illustrates that the button 34 can be translated 220, as shown by arrow, to a configuration to produce aspiration and irrigation. The button 34 can directly (as shown) or indirectly (e.g., via a control mechanism such as a valve 10 attached to a servomotor) close the controlled exhaust line 210. The flow can be the same as shown in FIG. 31 except that substantial positive pressure can be routed through the irrigant pressure line 22. The irrigant 57 can be forced through the irrigant channel 24, into the atomization port 46, mixed with the atomization gas, and sprayed out as atomized irrigant 68. Excessive pressure in the irrigant pressure line 22 can be released as exhaust flow 206, as shown by arrow.

The device 2 can be configured to prevent the irrigant 57 from the irrigant reservoir 54 from flowing solely from the application of pressure in the aspirant pressure line 18 or aspirant channel 26. For example, the irrigant reservoir 54 can be locked closed (e.g., preventing any irrigant 57 from exiting the irrigant reservoir 54) by a locking valve (e.g., piston 124 or syringe) when the device 2 is configured to not irrigate (e.g., the irrigation control 32 is set to "off"). When the device 2 is configured to not irrigate, excess pressure from the aspirant pressure line 18 and/or aspirant channel and/or the negative pressure side of the pump 8 can be exhausted out of the device 2.

FIG. 41 illustrates that the device 2 can have a first valve 208 and/or a second valve 224. The first valve 208 can be between the pump 8 and the atomization channel 20 and/or irrigant pressure line 22 and an exhaust port 144. The second valve 224 can be between the pump 8 and the aspirant pressure line 18 and an intake port 152. Intake flow 310 can flow into intake port 152. The first 208 and second valves 224 can be in the same housing or separate housings. The valves can act as switches for routing the air pressure to and from the pump 8. The button 34 and valve spring 226 can control the position of the valve channel 228.

FIG. 42 illustrates that the first valve 208 can be in a first configuration to direct the flow from the pump 8 to the exhaust port 144 and to obstruct flow from the pump 8 to the atomization channel 20 and/or irrigant pressure line 22. The button 34 can be up and the valve spring 226 can be expanded. Flow from the pump 8 to the exhaust port 144 can flow through the valve channel 228. Flow from the pump 8 to the atomization channel 20 and/or irrigant pressure line 22 can be blocked by the first valve 208. The irrigant delivery pressure can be shut off completely or partially.

FIG. 43 illustrates that the first valve 208 can be in a second configuration to direct the flow from the pump 8 to the atomization channel 20 and to obstruct flow from the pump 8 to the exhaust port 144. The button 34 can be down and the valve spring 226 can be compressed. Flow from the pump 8 to the atomization channel 20 and/or irrigant pressure line 22 can flow through the valve channel 228. Flow from the pump 8 to the exhaust port 144 can be blocked by the first valve 208. The irrigant delivery pressure can be turned on completely or partially. The irrigant delivery pressure can be, for example, from about 80 mm Hg (1.5 psi) to about 120 mm Hg (2.32 psi).

The second valve 224 can have multiple configurations, similar to the first and second configurations shown for the first valve 208 in FIGS. 42 and 43. For example, the second valve 224 can have a first configuration to direct flow to the pump 8 from the aspirant pressure line 18 or to the pump 8 from the intake port 152.

The first valve 208 and/or the second valve 224 can be manually or automatically controlled. The first 208 and/or second valves 208 can be bimodal (e.g., on or off positions only), multimodal (e.g., fixed finite valve settings), analog (e.g., substantially infinite variability of valve settings), or a combination thereof.

Figure 44:
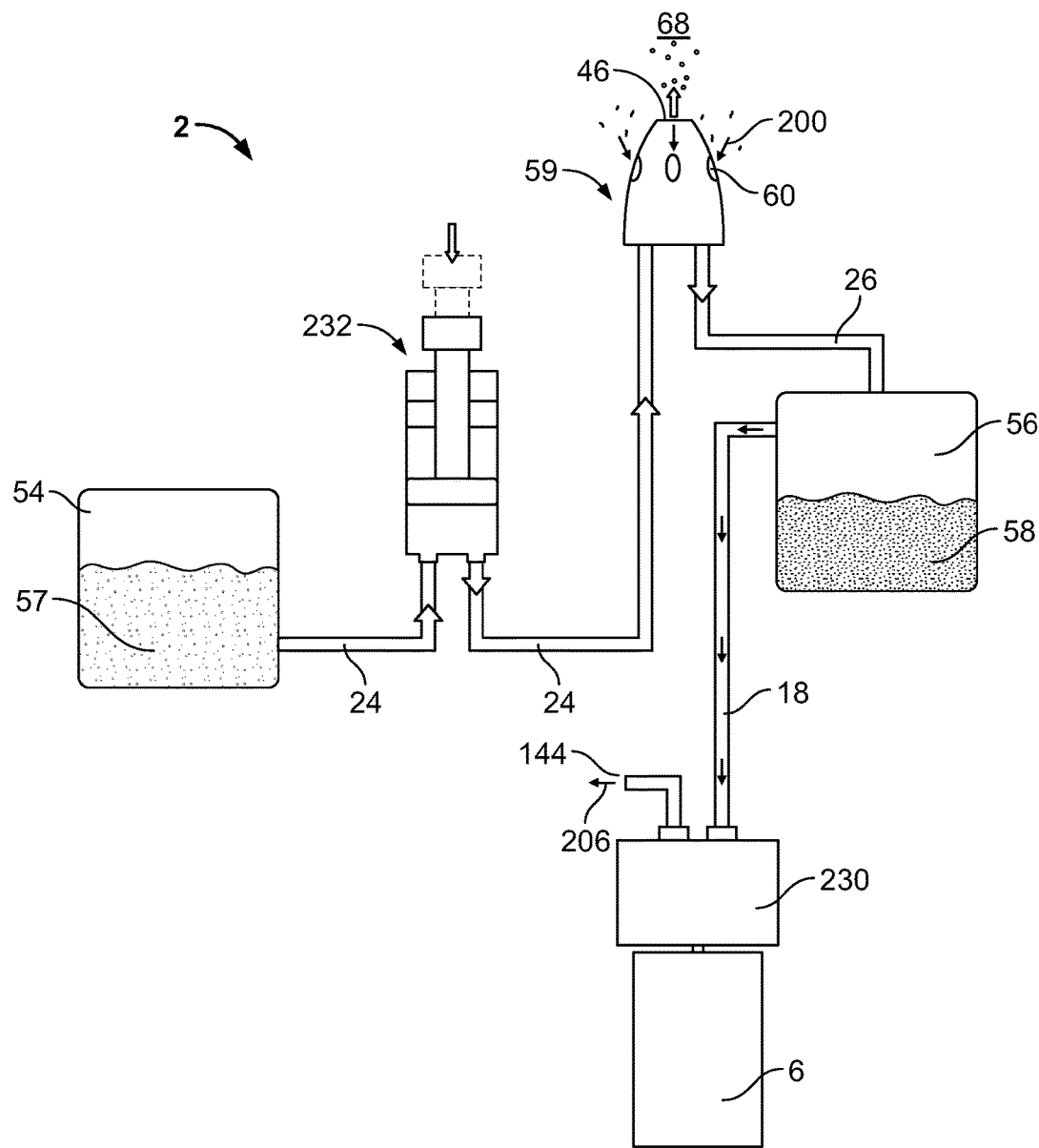

FIG. 44 illustrates that the device 2 can have a first pump 230 and a second pump 232. The first pump 230 and/or second pump 232 can be manual or automatic (e.g., driven by an electric motor). For example the first pump 230 can be automatic and the second pump 232 can be manual, spring-loaded piston pump with a one-way valve, as shown. The first pump 230 can provide aspirant suction pressure to the aspirant pressure line 18. The outgoing pressure from the first pump 230 can be exhausted through the exhaust port 144.

The second pump 232 can be in the irrigant channel 24. The second pump 232 can pressurize the irrigant 57 in the irrigant channel 24. The second pump 232 can be pumped, as shown by arrow, for example by hand (e.g., with a thumb on a button). The second pump 232 can be actuated by a thumb 42 on a button 34 on the body 4 of the device 2. The irrigant 57 can be atomized, as shown, upon exiting the atomization port 46. The irrigant 57 can be delivered from the nozzle 59 in a non-atomized stream or spray.

The pumps 8 can have bellows.

The first pump 230 can produce a different or the same flow rate and/or pressure as the second pump 232.

Figure 45:
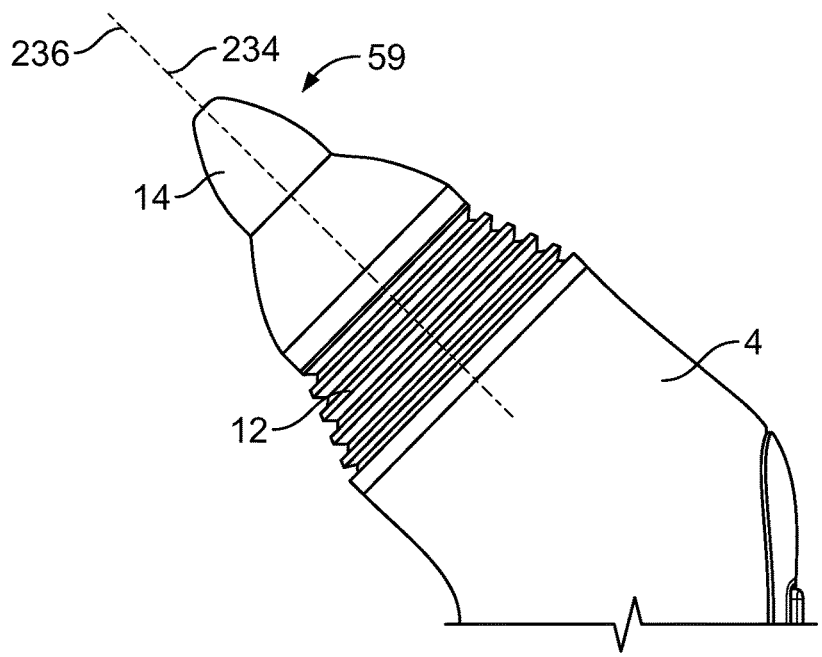
FIGS. 45 through 47 illustrate a distal portion of a variation of the irrigation and aspiration device showing the articulating neck in various configurations.

FIG. 45 illustrates that the head 14 can have a longitudinal head axis 234. The body 4 can have a longitudinal body axis 236 aligned with the head-end of the body 4. The head axis 234 can be aligned with the body axis 236, for example, when the head 14 is in a relaxed configuration and/or when the neck 12 is in a relaxed configuration.

Figure 46:
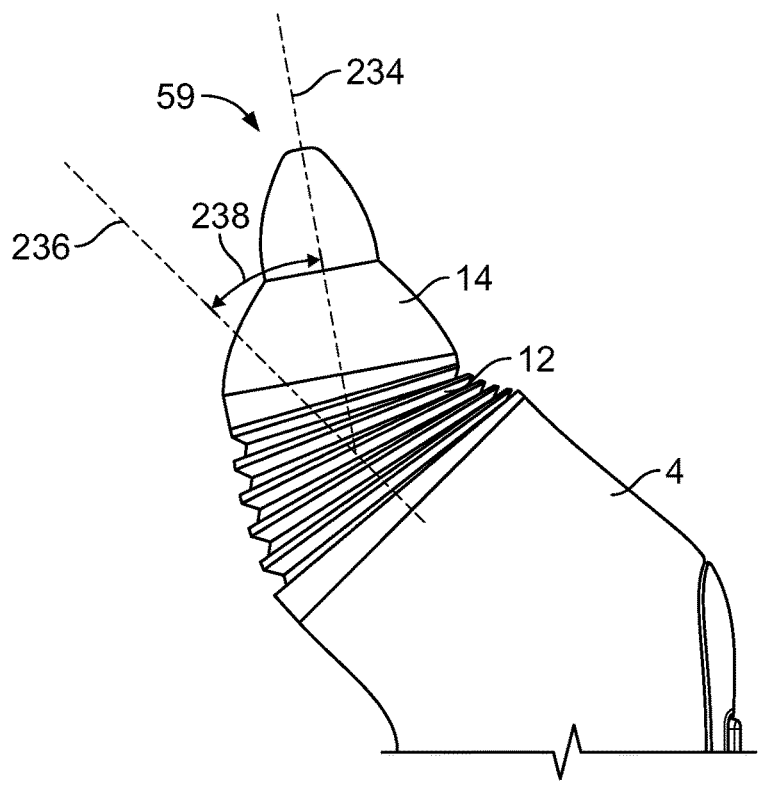

FIG. 46 illustrates that the head 14 can be rotated to a non-zero and positive head angle 238. The head angle 238 can be the angle from the body axis 236 to the head axis 234. The head angle 238 between the head axis 234 and the body axis 236 can be from about −180° to about +180° (e.g., the head 14 can have about 360° of rotational motion in one plane), for example about +35°, or 0°, or −35° (e.g., the head 14 can have about 70° of rotational motion in one plane). The neck 12 can be configured to deform to the rotated head angle 238. The neck 12 can resiliently reset to a preset head angle 238 (e.g., 0°) when a rotating force on the head 14 is removed.

Figure 47:
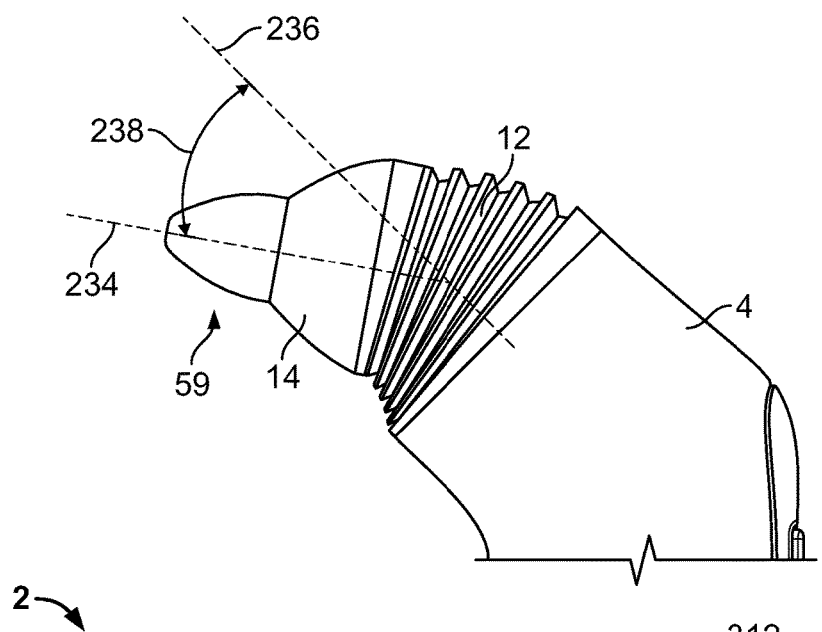

FIG. 47 illustrates that the head 14 can be rotated to a negative head angle 238.

Figure 48:
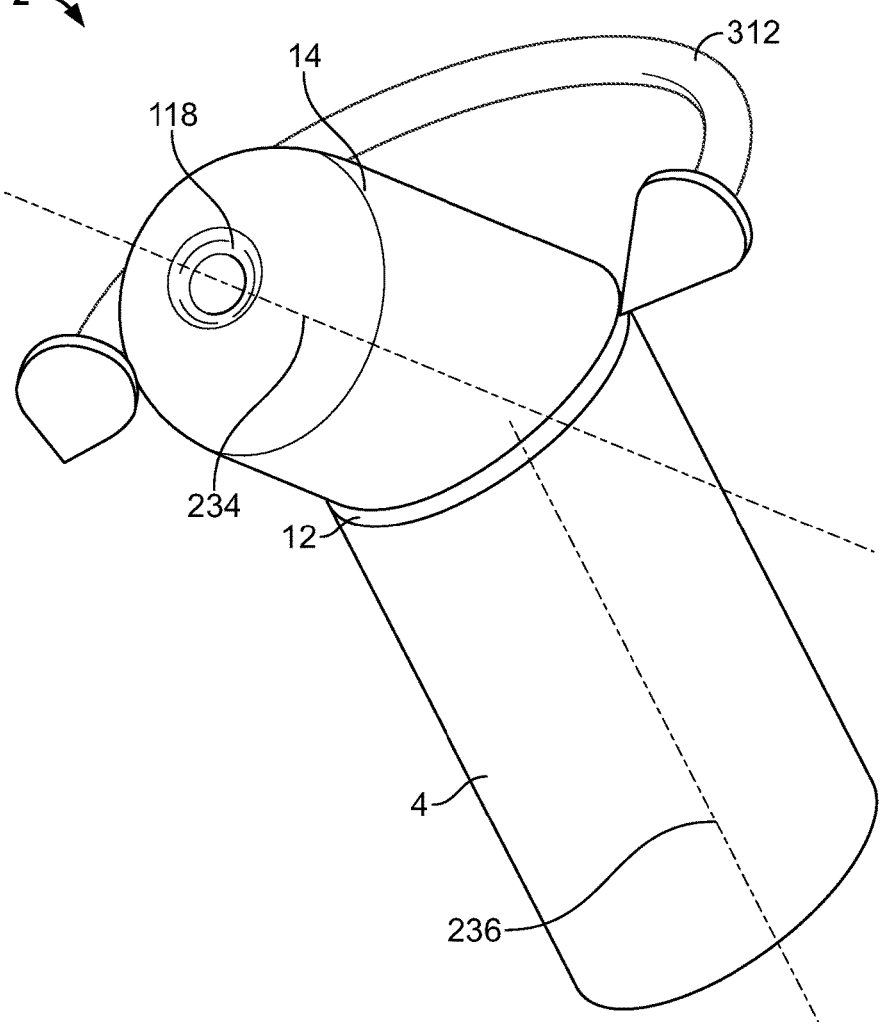
FIG. 48 illustrates a variation of a method of using a variation of the irrigation and aspiration device with the articulating neck.

FIG. 48 illustrates that the head 14 can rotate, as shown by arrow 312, around the body 4. For example, the head axis 234 can rotate around the body axis 236. The neck 12 can rotate the head 14 around the body 4.

The oscillations or vibrations of the device (e.g., due to pump motors, reciprocating solenoids, piezoelectric transducers) can be dampened. Actuators, pumps 8, valves 10 and other moving parts can be mounted to the body 4, neck 12 or head 14 using dampers, such as soft rubber washers. Excessive pressure and pump exhausts can be muffled, for example using a restricting plate in an exhaust conduit 140 or port 144. The walls of the device 2 can be thickened and made from layered and/or laminated materials. The walls of the device 2 can be otherwise sound-proofed. Moving parts in the device 2 can be dynamically balanced, for example such that all support forces sum to zero at any given instant and/or the device 2 can have active noise cancellation. Motors (e.g., in the pumps) can have counterbalances. Multiple motors can be configured to oppose dynamic forces.

Any of the valves 10 herein can be flow diodes, such as check valves 10. Any of the valves 10 herein can be ball valve, swing valve, clapper valve, umbrella valve, double check valve, duck bill valve 70, or combinations thereof.

The device 2 can be configured at full power to aspirate, for example, up to about 20,000 cc/min. (1,220 in$^3$/min.) of air with no flow restriction. The device 2 can be configured to at full power to produce an aspiration suction with no flow, for example, up to about 100 mmHg (2 psi). The device 2 can be configured at full power to irrigate up to about 1.5 cc/min. (9.2 in$^3$/min.) of irrigant 57 with no flow restriction.

The device 2 can be configured to be portable. For example, the device 2 can be unattached to any external devices (e.g., a wall or floor-mounted outlet or source for power, pressure, irrigant, or the aspirant reservoir).

The device 2 can be configured to be handheld. For example, the device 2 can weigh less than about 5.0 kg (11 lbs.), more narrowly less than about 2.0 kg (4.4 lbs.), more narrowly less than about 1.0 kg (2.2 lbs.). The device 2 can have a total maximum diameter less than about 41 cm (16 in.), more narrowly less than about 30 cm (12 in.), yet more narrowly less than about 25 cm (10 in.).

The device 2 can be used to deliver therapeutic drugs, and/or saline, and/or diagnostic agents, and/or antiseptic agents. The device 2 can be used to delivery drugs to the lungs.

The device 2 can have one, two or more buttons 34, rocker switches, or other elements to control the aspirant suction pressure and/or irrigant delivery pressure. The buttons 34 (or other elements) can be used to activate electronics (e.g., the pump motor, microprocessor), valves, manually pump, or combinations thereof.

The terms aspiration and aspirant are used interchangeably herein when used as descriptors for elements (e.g., aspiration reservoir 56 and aspirant reservoir 56). The terms irrigation and irrigant are used interchangeably herein when used as descriptors for elements. The terms atomizing and atomization are used interchangeably herein when used as descriptors for elements.

Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the invention, and variations of aspects of the invention can be combined and modified with each other in any combination.

We claim:

1. A portable, handheld device for irrigating with an irrigant and aspirating biological tissue and/or secretions comprising:
   a body;
   a first channel having a first port, the first channel removably connectable to the body;
   a second channel having a second port, the second channel removably connectable to the body;
   a first reservoir removably connectable to the body;
   a second reservoir removably connectable to the body; and
   a control, wherein the control has a first configuration and a second configuration, wherein when the control is in the first configuration, an aspiration is activated, wherein when the control is in the second configuration, an irrigation is activated, and wherein the aspiration is controllable concurrently with the irrigation, wherein the first reservoir is in fluid communication with the first port when the first reservoir is removably connected to the body and when the control is in the first configuration, and wherein the second reservoir is in fluid communication with the second port when the second reservoir is removably connected to the body and when the control is in the second configuration.

2. The device of claim 1, wherein when the control is in the second configuration, the irrigation is controllable concurrently with the aspiration by a fluid control system.

3. The device of claim 1, wherein when the control is in the second configuration, the irrigation is activated concurrently with the aspiration by a fluid control system.

4. The device of claim 1, wherein the control is sequentially manipulatable from a non-activated state to the first configuration and then to the second configuration, and wherein when the control is in the second configuration, the irrigation is activated concurrently with the aspiration by a fluid control system.

5. The device of claim 1, wherein the control comprises a first switch and a second switch, wherein when the control is in the first configuration the first switch is in an activated state, and wherein when the control is in the second configuration the second switch is in an activated state.

6. The device of claim 5, wherein the first switch controls the irrigation and the second switch controls the aspiration.

7. The device of claim 6, wherein the first and second switches are simultaneously controllable.

8. The device of claim 1, wherein the control comprises a single press-button, wherein the single press-button position controls the configuration of the control.

9. The device of claim 1, wherein at least a length of the first channel is nonparallel with at least a length of the second channel.

10. A portable, handheld device for irrigating with an irrigant and aspirating biological tissue and/or secretions comprising:
    a body;
    a head having a first port and a second port, wherein the head is removably connectable to the body, and wherein at least a portion of the head comprises a compliant surface configured to seal against a nostril;
    a first reservoir removably connectable to the body;
    a second reservoir removably connectable to the body;
    a first channel comprising a head first channel and a body first channel, wherein the head first channel terminates at the first port, and wherein the head first channel is in fluid communication with the body first channel when the head is removably connected to the body;
    a second channel comprising a head second channel and a body second channel, wherein the head second channel terminates at the second port, and wherein the head second channel is in fluid communication with the body second channel when the head is removably connected to the body;
    a control configured to activate an aspiration and an irrigation, wherein the control has a first configuration and a second configuration, wherein when the control is in the first configuration, the aspiration is activated, wherein when the control is in the second configuration, the irrigation is activated, and wherein the aspiration and the irrigation are simultaneously activatable, wherein the first reservoir is in fluid communication with the first port when the first reservoir is removably connected to the body and when the control is in the first configuration, and wherein the second reservoir is in fluid communication with the second port when the second reservoir is removably connected to the body and when the control is in the second configuration.

11. The device of claim 10, wherein when the control is in the second configuration, the irrigation is controllable concurrently with the aspiration.

12. The device of claim 10, wherein when the control is in the second configuration, the irrigation is activated concurrently with the aspiration.

13. The device of claim 10, wherein the control is sequentially manipulatable from a non-activated state to the first configuration and then to the second configuration, and wherein when the control is in the second configuration, the irrigation is activated concurrently with the aspiration.

14. The device of claim 10, wherein the control comprises a first switch and a second switch, wherein when the control is in the first configuration the first switch is in an activated state, and wherein when the control is in the second configuration the second switch is in an activated state.

15. The device of claim 14, wherein the first switch activates the aspiration when the control is in the first configuration and the second switch activates the irrigation when the control is in the second configuration.

16. The device of claim 15, wherein the first and second switches are simultaneously controllable.

17. The device of claim 10, wherein the control comprises a single press-button, wherein the single press-button position controls the configuration of the control.

18. The device of claim 10, wherein the head is rotatable with respect to the body, and wherein at least a length of the head first channel is nonparallel with at least a length of the head second channel.

19. A portable, handheld device for irrigating with an irrigant and aspirating biological tissue and/or secretions comprising:
    a body;
    a head having an irrigant port and an aspirant port, wherein the head is removably connectable to the body, and wherein at least a portion of the head comprises a compliant surface configured to seal against a nostril;
    an irrigant reservoir removably connectable to the body;
    an aspirant reservoir removably connectable to the body;
    an irrigation channel comprising a head irrigation channel and a body irrigation channel, wherein the head irrigation channel terminates at the irrigant port, and wherein the head irrigation channel is in fluid communication with the body irrigation channel when the head is removably connected to the body;
    an aspiration channel comprising a head aspiration channel and a body aspiration channel, wherein the head aspiration channel terminates at the aspirant port, and wherein the head aspiration channel is in fluid communication with the body aspiration channel when the head is removably connected to the body;
    a control configured to control an aspiration pressure and an irrigation pressure, wherein the control has a first configuration and a second configuration, wherein when the control is in the first configuration, the aspiration pressure is controlled, wherein when the control is in the second configuration, the irrigation pressure is controlled, and wherein the aspiration pressure and the irrigation pressure are simultaneously controllable, wherein the aspirant reservoir is in fluid communication with the aspirant port when the aspirant reservoir is removably connected to the body and when the control is in the first configuration, and wherein the irrigant reservoir is in fluid communication with the irrigant port when the irrigant reservoir is removably connected to the body and when the control is in the second configuration.

20. The device of claim 19, wherein the control comprises a first switch and a second switch, wherein when the control is in the first configuration the first switch is in an activated state, wherein when the control is in the second configuration the second switch is in an activated state, wherein the first switch activates the aspiration pressure when the control is in the first configuration and the second switch activates the irrigation pressure when the control is in the second configuration, and wherein the first and second switches are simultaneously controllable.

* * * * *